(12) United States Patent
Jing et al.

(10) Patent No.: US 8,168,603 B2
(45) Date of Patent: May 1, 2012

(54) G-QUARTET OLIGONUCLEOTIDES THAT TARGET HYPOXIA-INDUCIBLE FACTOR 1-α (HIF1α)

(75) Inventors: Naijie Jing, Pearland, TX (US); Yongli Guan, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 389 days.

(21) Appl. No.: 12/117,877

(22) Filed: May 9, 2008

(65) Prior Publication Data

US 2009/0075928 A1    Mar. 19, 2009

Related U.S. Application Data

(60) Provisional application No. 60/917,083, filed on May 10, 2007.

(51) Int. Cl.
| | | |
|---|---|---|
| *C12N 15/11* | (2006.01) | |
| *C12Q 1/68* | (2006.01) | |
| *C07H 21/04* | (2006.01) | |
| *C12N 5/00* | (2006.01) | |

(52) U.S. Cl. ............ 514/44 A; 435/6.17; 435/375; 536/23.1; 536/24.5

(58) Field of Classification Search .......... None
See application file for complete search history.

(56) References Cited

U.S. PATENT DOCUMENTS 7,119,078 B2 * 10/2006 Jing et al. ............ 514/44 R
2006/0199777 A1 * 9/2006 Jing et al. ............ 514/44

FOREIGN PATENT DOCUMENTS

WO    WO 02/076469    * 10/2002

OTHER PUBLICATIONS

International Preliminary Report on Patentability, issued Nov. 10, 2009 (published Nov. 10, 2009) during the prosecution of International Application No. PCT/US2008/063172.
De Armond et al., "Evidence for the presence of a guanine quadruplex forming region within a polypurine tract of the hypoxia inducible factor 1 alpha promoter," Biochemistry. Dec. 13, 2005; vol. 44(49):16341-50.
Jing et al., "G-quartet oligonucleotides: a new class of signal transducer and activator of transcription 3 inhibitors that suppresses growth of prostate and breast tumors through induction of apoptosis," Cancer Res. Sep. 15, 2004; vol. 64(18):6603-9.
Xu et al., "Targeting Stat3 blocks both HIF-1 and VEGF expression induced by multiple oncogenic growth signaling pathways," Oncogene. Aug. 25, 2005; vol. 24(36):5552-60.
International Search Report issued Aug. 6, 2008 during the prosecution of International Application No. PCT/US08/63172.
Written Opinion issued Aug. 6, 2008 during the prosecution of International Application No. PCT/US08/63172.

* cited by examiner

*Primary Examiner* — Doug Schultz
(74) *Attorney, Agent, or Firm* — Fulbright & Jaworski L.L.P.

(57) ABSTRACT

The present invention concerns particular G-quartet oligonucleotides that are employed for the treatment and/or prevention of cancer. In specific cases, the G-quartet oligonucleotides inhibit HIF-1α.

16 Claims, 28 Drawing Sheets

G-QUARTET OLIGONUCLEOTIDES THAT TARGET HYPOXIA-INDUCIBLE FACTOR 1-α (HIF1α)

CROSS-REFERENCE TO RELATED APPLICATIONS

This application claims priority to U.S. Provisional Application Ser. No. 60/917,083, filed on May 10, 2007, and also to Chinese Patent Application Serial No. 200710142128.1, filed May 10, 2007, both of which applications are incorporated by reference herein in their entirety.

STATEMENT REGARDING FEDERALLY SPONSORED RESEARCH OR DEVELOPMENT

The present invention was developed using federal funds from the National Institutes of Health Grant NIH R01 Grant No. CA104035 and the National Institutes of Health SPORE development Grant Nos. CA58204 and CA97007. The United States Government has certain rights in the invention.

FIELD OF THE INVENTION

The present invention generally relates at least to the fields of molecular biology, cell biology, and medicine, in particular cancer. Specifically, the invention concerns methods and/or compositions for the treatment and/or prevention of cancer.

BACKGROUND OF THE INVENTION

Angiogenesis

A growing mass of tumor cells must recruit its own blood supply for maintenance of oxygen and nutrients, termed tumor angiogenesis (Duffy et al., 2003). Within tumors, the availability of $O_2$ and nutrients is limited by competition among actively-proliferating cells, and diffusion of metabolites is inhibited by high interstitial pressure (Duffy et al., 2003). In response to intratumoral hypoxia, angiogenesis-stimulating factors produced by tumor cells induce the formation of a new blood supply from the pre-existing vasculature, which is critical for tumor cells to survive and proliferate in a hostile microenvironment (Folkman, 1971; Zhong et al., 1999; Niedergethmann et al., 2000). Thus, hypoxia serves as a critical factor for both physiological and pathological angiogenesis.

The reasons why tumors become hypoxic remain unclear, but multiple mechanisms likely contribute to its development. These include at least the following: i) unrestrained growth and accelerated oxygen consumption by tumor cells; ii) poor lymphatic drainage of tumors resulting in high interstitial pressure, vascular collapse, and low pH; and/or iii) intratumoral shunting of oxygen-rich blood through immature vasculature. Also, tumor angiogenesis may not necessarily equate to tumor blood supply (Ikeda et al., 1999). Experimental evidence indicates that tumor cells exist under hypoxic conditions at a distance of 300-400 μm from blood vessels, indicating that hypoxic conditions are generally established in tumors measuring only 0.5 mm in diameter (Khan et al., 2002).

HIF-1α as a Critical Molecular Target for Cancer Therapy

Hypoxia is an important process in the progression and treatment resistance of many human cancers. Hypoxia-inducible factor-1 (HIF-1) plays crucial roles in tumor promotion by up-regulating its target genes, which are involved in metabolism, angiogenesis, cell survival, cell invasion, and drug resistance (Powis and Kirkpatrick, 2002; Hirota and Semenza, 2006). As a nuclear factor, HIF-1 was induced in hypoxic cells and bound to the cis-acting hypoxia response element (HER) located in the 3'-flanking region of the human EPO gene (Gatenby et al., 1998; Brahimi-Horn et al., 2001). HIF-1 is a heterodimeric transcription factor comprised of a HIF-1α subunit and a HIF-1β subunit (FIG. 2) (Brahimi-Horn et al., 2001). Both HIF-1 subunits belong to the basic helix-loop-helix (bHLH)-containing PER-ARNT-SIM (PAS)-domain family of transcription factors (Semenza and Wang, 1992). To date, more than 60 putative hypoxia-inducible genes have been found to be directly regulated by HIF-1. HIF-1α is the key protein, which determines the presence of HIF-1 and transcription of the hypoxia-inducible genes (Kowis and Kirkpatrick, 1992). Under normoxic conditions the cellular half-life of HIF-1α is around 5 minutes, as the protein is rapidly degraded by the ubiquitin-proteasome system (Wang and Semenza, 1995; Wang et al., 1995; Huang et al., 1998). Under hypoxic conditions, the HIF-1α protein is stabilized by absence of posttranslational hydroxylation event at residue P564 of the HIF-1α molecule (Huang et al., 1998). Hypoxic conditions led to HIF-1α stabilization and translocation to the cell nucleus, dimerization with HIF-1β to form the HIF-1 complex, and activation of transcription through HIF-1's binding to specific HREs in target sequences (Salceda and Caro, 1997). HIF-1α has been demonstrated to be overexpressed in many human cancers, including colon, breast, gastric, lung, skin, overian, prostate, renal and pancreatic carcinomas (Salceda and Caro, 1997; Semenza, 2003). Overexpression of HIF-1α in human cancers results in intratumoral hypoxia and genetic alternations, which associates with treatment failure and increased patient mortality (Semenza, 2003). HIF-1α mRNA expression was dramatically up-regulated in many human cancer specimens. Clinically, HIF-1α overexpression has been shown to be a marker of highly aggressive diseases and has been associated with poor prognosis and treatment failure in a number of cancers, including pancreatic carcinomas, prostate cancer, and others (Powis and Kirkpatrick, 2004; Hirota and Semenza, 2006). HIF-1α has been demonstrated to mediate hypoxia-induced VEGF expression in tumors leading to highly aggressive tumor growth (Semenza, 2003). Therefore, targeting HIF-1α is a useful therapeutic and/or preventative target for human cancers.

Regulation of HIF-1α Protein

The regulation of HIF-1α is shown in FIGS. 1 and 2: (i) growth-factors (GF), such as IGFR, EGFR, IL-1 and HER2, binding to a cognate receptor tyrosine kinase (RTK) activates the phophatidylinosttol 3-kinase (PI-3K) and mitogen-activated protein kinase (MAPK) pathways; and (ii) PI-3K is activated when growth factors are ligated in RTK. PI-3K phosphorylates and activates its downstream signaling pathways, such as a serine-threonine protein kinase (Akt). Then Akt activates mammalian target of rapamycin (mTOR) to increase HIF-1α synthesis. This pathway is negatively regulated by the PTEN tumor suppressor protein, which dephosphorylates the products of the PI-3K. In (iii), in the MAPK pathway, the extracellular-signal-regulated kinase (ERK) is activated by the upstream MAP/ERK kinase (MEK). ERK, in turn, activates MNK to increase the rate at which mRNAs within the cell including HIF-1α mRNA are translated into protein. (iv) Under normoxia conditions, HIF-1 prolyl hydroxylases (PHD) hydroxylate the prolyl residues at amino acid P402 and P564 and are then recognized by VHL and targeted to the ubiquitin prosteasome pathway. VHL binding is also promoted by acetylation of K532. $O_2$-dependent hydroxylation of $N_8O_3$ in HIF-1α requires the enzyme FIH-1

(factor inhibiting HIF-1). Hydroxylation of $N_8O_3$ during normoxia blocks the binding of p300 and CBP to HIF-1α and therefore inhibits HIF-1 mediated gene transcription. (v) Under hypoxia conditions, HIF-1α is not hydroxylated because the major substrate, dioxygen, is not available. The unmodified protein escapes the VHL-binding, ubiquitination, and degradation, and then dimerizes HIF-1α and stimulates the transcription of its target genes. When $N_8O_3$ is not asparaginyl-hydroxylated, p300 and CBP can bind to HIF-1α, allowing transcriptional activation of HIF-1 target genes, which are involved in many cell processes: angiogenesis, anti-apoptosis, metabolism, metastasis, and others (Semenza, 2003; Shi and Fang, 2004).

SUMMARY OF THE INVENTION

The present invention is directed to systems, compositions, and methods that are for cancer therapy and/or prevention for an individual. In particular cases, the invention concerns oligonucleotides that provide cancer therapy and/or prevention to an individual with any type of cancer. In specific embodiments, the invention is useful for prostate, pancreatic, lung, brain, breast, liver, colon, uterine, cervical, testicular, skin, bone, spleen, thyroid, stomach, anal, gall bladder, or esophageal cancer, for example. In specific embodiments, the individual is a mammal, such as a human, dog, cat, horse, pig, sheep, or goat, for example.

In certain embodiments the invention concerns compositions and methods for an individual that has cancer, has metastatic cancer, is suspected of having cancer, or is at high risk for developing cancer. The therapy of the invention may be delivered to the individual at any point of having cancer, and in specific embodiments the individual is also given an additional therapy for cancer. In particular cases, the additional therapy is delivered to the individual before the therapy/prevention composition/methods of the invention, after the therapy/prevention composition/methods of the invention, and/or during the therapy/prevention composition/methods of the invention. In certain cases the cancer is resistant to one or more therapies.

The oligonucleotides of the invention may consist of particular sequences or, in other aspects of the invention, there may be additional sequences in the oligonucleotides. In specific embodiments, the oligonucleotides consist of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In other embodiments, the oligonucleotides comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In still other embodiments, the oligonucleotides consist essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In particular embodiments, the oligonucleotides are isolated. In specific aspects, the oligonucleotides inhibit HIF1α expression and/or activity. In further embodiments, an anti-cancer agent(s) comprises one or more of the oligonucleotides of the invention.

Another embodiment of the present invention includes a method of inhibiting hyperproliferative cell growth comprising administering to the cell an effective amount of a G-rich oligonucleotide composition, wherein the composition modulates HIF1α, thereby inhibiting hyperproliferative cell growth. In specific embodiments, the hyperproliferative cell is a cancer cell, such as a tumor cell. For example, the cancer cell is a melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

Another embodiment of the present invention is a method of treating a hyperproliferative disease, such as cancer, comprising administering to an individual an effective amount of a G-rich oligonucleotide in an amount effective to treat the hyperproliferative disease. Yet further, the G-rich composition may be administered in combination with chemotherapy, immunotherapy, surgery, or radiotherapy. The composition comprises a lipid-oligonucleotide complex in certain embodiments.

In specific cases, the G-quartet oligonucleotides inhibit HIF-1α, and in particular cases the oligonucleotides inhibit the activity, function, and/or expression of HIF-1α. In specific embodiments, the inhibition of HIF-1α is a direct inhibition or an indirect inhibition.

In one embodiment of the present invention, there is a method of treating and/or preventing hyperproliferative disease in an individual, comprising delivering to the individual a therapeutically effective amount of one or more oligonucleotides, wherein said oligonucleotides comprise a G quartet and inhibit HIF1α. In specific embodiments, the oligonucleotides are further defined as comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and a combination thereof. In additional specific embodiments, the oligonucleotides are further defined as consisting essentially of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13. In further specific embodiments, the oligonucleotides are further defined as consisting of a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and a combination thereof.

In certain embodiments of the invention, the individual is delivered an additional cancer therapy, such as one that comprises chemotherapy, immunotherapy, radiation, surgery, or a combination thereof. In specific embodiments, the cancer is pancreatic cancer or prostate cancer.

In other embodiments of the invention, there is an isolated oligonucleotide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and a combination thereof.

In an additional embodiment of the invention, there is a kit comprising one or more oligonucleotides selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and a combination thereof. The kit may further comprise an additional anti-cancer agent, in specific embodiments.

In an additional embodiment of the present invention, there is a method of intracellular delivery of a G-rich oligonucleotide comprising the steps of denaturing the oligonucleotide, wherein the oligonucleotide is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and a combination thereof; mixing the oligonucleotide with a lipid to form an oligonucleotide-lipid complex; and incubating the oligonucleotide-lipid complex with a cell, wherein the oligonucleotide is internalized into the cell. In specific aspects, the internalized oligonucleotide is induced to form a G-quartet structure. In further specific aspects, the G-quartet structure enters the nucleus. In additional specific aspects, the G-quartet structure inhibits HIF1α expression and/or activity.

In one embodiment of the invention, there is an isolated oligonucleotide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or a combination thereof.

Accordingly, oligonucleotides that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% to about 90%; or even more preferably, between about 91% and about 99%; of bases that are identical or functionally equivalent to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 will be sequences that are biologically functional equivalents provided the biological activity of the oligonucleotide is maintained.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
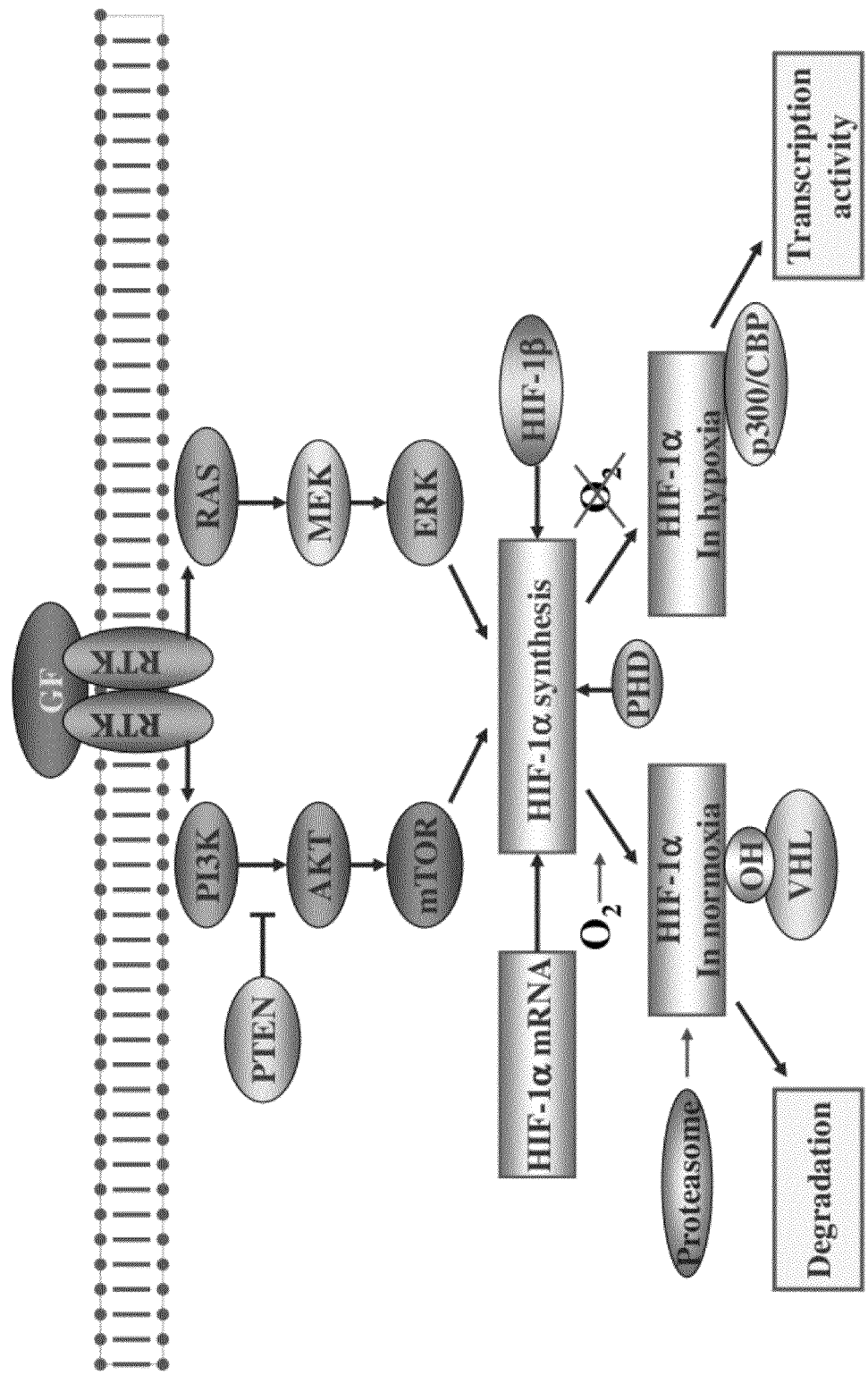
FIG. 1 illustrates an exemplary pathway of synthesis and regulation of HIF-1α.

It is readily apparent to one skilled in the art that various embodiments and modifications can be made to the invention disclosed in this Application without departing from the scope and spirit of the invention.

The present application incorporates by reference herein in its entirety U.S. Pat. No. 7,119,078.

I. Definitions

As used herein, the use of the word "a" or "an" when used in conjunction with the term "comprising" in the sentences and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The term "base" as used herein includes both the deoxyribonucleic acids and ribonucleic acids. The following abbreviations are used. "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill would readily recognize that these bases may be modified or derivatized to optimize the methods of the present invention. In addition, bases can refer to unnatural (synthetic) bases used in place of an A, C, T, or G.

As used herein the term "effective amount" is defined as an amount of the agent (such as the oligonucleotide or a combination of the oligonucleotide and an other agent) that is sufficient to detectably inhibit growth or proliferation of a cell, including a cancer cell.

The term "cancer" as used herein is defined as a hyperproliferation of cells whose unique trait—loss of normal control—results in unregulated growth, lack of differentiation, local tissue invasion, and/or metastasis. Examples include but are not limited to, breast cancer, prostate cancer, ovarian cancer, cervical cancer, skin cancer, pancreatic cancer, colorectal cancer, renal cancer and lung cancer.

The term "hyperproliferative disease" is defined as a disease that results from a hyperproliferation of cells. Exemplary hyperproliferative diseases include, but are not limited to, cancer or autoimmune diseases. Other hyperproliferative diseases may include vascular occlusion, restenosis, atherosclerosis, or inflammatory bowel disease, for example.

The term "oligonucleotide" as used herein is defined as a molecule comprised of two or more deoxyribonucleotides or ribonucleotides, preferably more than ten. Its exact size will depend on many factors including the specificity of the oligonucleotide. In addition, bases can refer to unnatural (synthetic) bases used in place of an A, C, T or G.

The term "therapeutically effective amount" as used herein is defined as the amount of a molecule or a compound required to improve at least one symptom associated with a disease. For example, in the treatment of cancer, a molecule or a compound that decreases, prevents, delays or arrests any symptom of the cancer is therapeutically effective. A therapeutically effective amount of a molecule or a compound is not required to cure a disease but will provide a treatment for a disease. A molecule or a compound is to be administered in a therapeutically effective amount if the amount administered is physiologically significant. A molecule or a compound is physiologically significant if its presence results in technical change in the physiology of a recipient individual.

The term "treatment" as used herein is defined as the management of a medical condition (such as hyperproliferative disease, including cancer, for example) of an individual through medical or surgical means. The treatment improves or alleviates at least one symptom of a medical condition or disease and is not required to provide a cure.

The term "sample" as used herein indicates a sample from an individual containing at least one cancer cell, including at least one tumor cell. Tissue or cell samples can be removed from almost any part of the body. The most appropriate method for obtaining a sample depends on the type of cancer that is suspected or diagnosed. Biopsy methods include needle, endoscopic, and excisional, for example.

Any of the methods described herein may be implemented using therapeutic compositions of the invention and vice versa. It is contemplated that any embodiment discussed with respect to an aspect of the invention may be implemented or employed in the context of other aspects of the invention.

II. Oligonucleotides

Generally, the oligonucleotides of the present invention may have any percentage of guanosine bases that will allow for tetrad formation, in specific embodiments. In specific embodiments, the oligonucleotides of the present invention comprise a percentage of guanosine bases. In particular aspects, the guanosine is important in forming tetrads that stabilize the three-dimensional structure of the oligonucleotides. Thus, the oligonucleotides of the present invention may comprise or contain two or more segments of two or more guanosine bases, and an overall high percentage of G in order to enable the oligonucleotide to form at least one guanosine tetrad. In specific embodiments, the range of the residues of the G quartet oligonucleotides (GQ-ODNs) is from 14-mers (e.g. JG-ODNs) to 24-mers (e.g. T40216). In 14-mer GQ-ODNs, at least there are 8 G residues (8 to 11, for example) (57%-79%), however, in 24-mer (T40216) there are 20 G-residues (83%) in certain cases. In a specific embodiment of the invention, the G-quartet ODN comprises at least two G-quartet (8 G residues) plates in the middle of their structure. For example, 14-mers have only two G-quartet plates and T40216 has 4 G-quartet plates in the middle of its structure. T40214 is an exemplary 16-mer with two G-quartets in the middle and 4 Gs in loop domains, so it comprises 12 G-residues (75%). In specific embodiments, the percentage of Gs in the oligonucleotide are at least 50%, 55%, 60%, 65%, 70%, 75%, 80%, 85%, 90%, 95%, 97% or 100%.

In particular embodiments of the invention, the oligonucleotides are no less than 8 nucleotides, for example, no less than 9, no less than 10, no less than 11, no less than 12, no less than 13, no less than 14, no less than 15, no less than 16, no less than 17, no less than 18, no less than 19, or no less than 20. In other particular embodiments of the invention, the oligonucleotides are, for example, no more than 8 nucleotides, no more than 9 nucleotides, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, no more than 28, no more than 29, or no more than 30. In certain aspects, the oligonucleotide is from 11 to 19 nucleotides, from 12 to 14 nucleotides, from 12 to 15 nucleotides, from 12 to 16 nucleotides, from 12 to 17 nucleotides, from 13 to 14 nucleotides, from 13 to 15 nucleotides, from 13 to 16 nucleotides, from 13 to 17 nucleotides, from 14 to 15 nucleotides, from 14 to 16 nucleotides, from 14 to 17 nucleotides, from 14 to 18 nucleotides, from 14 to 19 nucleotides, from 14 to 20 nucleotides, from 14 to 21 nucleotides, from 14 to 22 nucleotides, from 14 to 23 nucleotides, from 14 to 24 nucleotides, from 15 to 16 nucleotides, from 15 to 17 nucleotides, from 15 to 18 nucleotides, from 15 to 19 nucleotides, from 16 to 17 nucleotides, from 16 to 18 nucleotides, or from 16 to 19 nucleotides, for example.

In specific embodiments, the oligonucleotides include, but are not limited to, at least one or more of the following sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In certain cases, the oligonucleotides are provided to an individual in a reagent, which may be termed a pharmaceutical carrier, in certain embodiments of the invention.

III. Exemplary Intracellular Delivery System

The present invention in certain aspects is drawn to methods to deliver G-rich oligonucleotides into a cell and specifically into the nucleus of the cell. The novel intracellular delivery system of the present invention is based upon the property of potassium-induced formation of the G-quartet structure. It is also contemplated that the G-rich oligonucleotides may be used as therapeutic agents to treat hyperproliferative diseases, such as cancer. The G-rich oligonucleotides are designed to inhibit the function of at least one target protein through indirect or direct binding interaction, which is different from antisense oligonucleotides, for example, that act as a template through hybridization to target a specific mRNA or DNA to inhibit gene expression at the level of transcription or translation.

A specific embodiment of the present invention is a method of intracellular delivery of a G-rich oligonucleotide comprising the steps of denaturing the oligonucleotide; mixing the oligonucleotide with a lipid to form an oligonucleotide-lipid complex; and incubating the oligonucleotide-lipid complex with a cell, wherein the oligonucleotide is internalized into the cell. In specific embodiments, the internalized oligonucleotide is induced to form a G-quartet structure. In a further embodiment, the G-quartet structure enters the nucleus. The G-quartet structure inhibits HIF-1α in particular embodiments. More specifically, the G-quartet is or comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and/or SEQ ID NO:13.

In certain embodiments, a G-rich oligonucleotide forms a stable and symmetric intramolecular G-quartet structure with about 15 Å width and 15 Å length in the presence of $K^+$ ions (Jing and Hogan, 1998). This structure seems to resemble a cylinder with positive charges inside and negative charges on the surface. The net charge on complex is most likely to be close to a neutral zwitterion under physiologic conditions.

The present invention provides a method of intracellular delivery of a G-rich oligonucleotide. In certain embodiments, the method comprises denaturing the oligonucleotide; mixing the oligonucleotide with a lipid to form an oligonucleotide-lipid complex; and incubating the oligonucleotide-lipid complex with a cell, wherein the oligonucleotide is internalized into the cell.

It is contemplated that the oligonucleotide is mixed with a lipid to form a lipid-oligo or lipid-DNA complex. One of skill in the art is aware that oligonucleotide and DNA are interchangeable.

In the present invention, the delivery system is based upon the property of potassium dependent formation of G-quartet structure. The difference of $K^+$ concentrations inside and outside cells are used to induce the molecules of G-rich oligonucleotides forming different structures inside and outside cells. It is well known and understood by those of skill in the art that the K+ ion concentration is 4 mM outside cells and 140 mM inside cells. Thus, the G-quartet is designed to stay in an unfolded structure in 4 mM K+ and to fold in an environment containing 140 mM $K^+$.

According to the present invention, intracellular delivery of G-quartet oligonucleotides by DNA-lipid complexes can be divided into three steps: (1) binding and internalization of DNA by the cells, (2) escape of the DNA into the cytoplasm, and (3) entry of the DNA oligos into the nucleus. The primary driving force for the binding of the lipid-DNA complex to the cell membrane is electrostatic (Maurer et al., 1999; Chesnoy and Huang, 2000).

It is contemplated that the internalization of the lipid-DNA occurs mainly through endocytosis. The release of DNA oligonucleotides into the cytoplasm is most likely caused by the interaction between the cationic lipid and anionic molecules presented in the membrane. Thus, variation of the charge ratio, incubation time or the component of lipids can increase the percentage and speed of DNA oligonucleotides released from lipid-DNA complexes.

Yet further, the G-quartet oligonucleotides of the present invention enter the nucleus of the cell in particular aspects. The main reason that the refolded G-quartet molecules can penetrate into nucleus is considered to be due to their structural characters. After the oligonucleotide molecules are released from lipid-DNA complexes and enter the cytoplasm, they refold to form G-quartet structures due to the influence of K+ ions inside the cells. The highly stable and compact G-quartet structure greatly enhances the ability of the oligonucleotides to resist nuclease digestion (Jing, 2000). Thus, the reformed G-quartet structure has a greater capacity to penetrate into the nucleus through the nuclear pores.

A. Using Other Drug-Carriers to Characterize Other Vehicles than PEI for JG-ODN Delivery This exemplary approach was designed based upon the physical characteristics of G-quartet ODNs and its delivery system (Jing et al., 2002). G-quartet oligonucleotides with special characteristics—a low capacity for aggregation and overall neutrality—have a weak tendency to incorporate with liposomes. G-quartet ODNs also cannot directly penetrate into cells through cell membranes. Thus, the inventors have developed a novel intracellular delivery system for G-quartet ODNs (Jing et al., 2002; Jing et al., 2003). Recently, polymeric nano-particles have been considered as promising carriers for anti-cancer agents since nanopaticles can provide a more efficient and less harmful drug delivery. Thus, in specific embodiments nano-polymers are employed as drug carriers, such as poly(lactic-co-glycolic acid) (PLGA) and its analog, PLGA-pDNA, for example (Mittal et al., 2007; Cohen et al., 2000).

Methods to identify an effective drug carrier have been established (Jing et al., 2002; Jing et al., 2003). Briefly, there are several steps:

(1) JG-ODNs incorporating with drug-carriers. (i) Run non-denaturing gels of vehicle-ODN complexes using $^{32}$P-labeled ODNs and different drug carriers, including PEI (a polymer, 25,000), PLGA (a nano-particles, 45,000 or 85,000) or PLGA analogs (e.g. PLGA-pDNA), for example, at different ratios of vehicle/ODN. The gel will show two bands: one is composed of the vehicle-ODN complex (slow migration) and another is free ODN without incorporating with vehicles (fast migration) (Ting et al., 2002). (ii) Analyze the intensities of the bands of vehicle-ODN complex and free ODN to estimate the percentage of incorporation between the ODNs and carriers and determine the best ratio for drug delivery.

(2) Measure the delivery efficiency for each vehicle-ODN complex in cells. (i) First, adding the vehicle/$^{32}$P-ODN at designed ratio into cancer cells. (ii) After 3 hours in culture, the cells are washed twice with fresh medium to remove free vehicle/ODN complex, and the cells continue to be incubated for 24 hours. (iii) Then $^{32}$P-labeled ODNs are extracted from lysed cells and run on non-denaturing gels. (iv) The gel will show two bands: one is unreleased ODNs with vehicles (slow migration) and another is released ODNs in cytoplasm (fast migration). The band intensities of ODNs obtained from lysed cells demonstrates the delivery efficiency of the tested vehicle (Jing et al., 2002; Ting et al., 2003).

(3) Microscopy. (i) Incubate 5'-fluorenscent-labeled JG-ODNs with PEI (or PLGA) at designed ratio in room temperature for 1 hour and then add 700 ng of the PEI/ODN complexes to cell plates. (ii) After cultured 3 hours for delivery, the cell wells are washed three times with fresh medium to remove free ODNs and free PEI/ODN complex, so that only the delivered complexes are continued to be incubated within cells at 37° C. for 24 hours. (iii) Remove the cell culture medium and wash the plates three times with PBS again. Then lyse the cells for 2 minutes by adding 0.5% Triton and fix the lysed cells on slides for 15 minutes in 3.7% formaldehyde. (iv) Wash the cells three times with PBS to eliminate free fluorescence. Identify the labeled JG-ODNs under microscopy (400× magnification) (Jing et al., 2003). (v) Combining the results obtained from steps (1) through (3), one can identify effective drug carriers for ODNs.

B. Determining the Best Ratio of ODN/Vehicle for JG-ODN Administration in Vivo

The efficiency of drug administration in vivo is a critical factor for drug optimization. Weak drug activity in vivo may be due to low effective drug delivery, in particular aspects. To enhance drug activity in xenograft tumors, one can perform in vivo delivery experiments to determine the best ratio of ODN/vehicle (PEI or a nano-carrier) for delivering JG-ODNs in vivo.

A suitable ratio of ODN/PEI for JG-ODNs in vivo is determined. Theoretically, intracellular delivery of ODN/PEI complexes can be divided into three steps:

(1) Binding of DNA oligonucleotides to the cells. The primary driving force for the binding of the PEI-DNA complex to the cell membrane is electrostatic (Maurer et al., 1999; Chesnoy et al., 2000). The internalization of the PEI-DNA occurs mainly through endocytosis. The main differences in binding efficiency between different vehicle and DNA are related to their physical properties, such as stability, size and charge density, in specific aspects. The charge ratio between cationic PEI and DNA and the duration of incubation are parameters for delivery efficiency. Usually, an increase in the charge ratio and incubation time will result in higher delivery efficiency, in certain embodiments.

(2) Escape of the DNA oligonucleotides into the cytoplasm. DNA is released into the cytoplasm in specific embodiments by disruption of the endosomal membrane, caused by the interaction between cationic PEI and anionic ODNs present in the membrane. The disruption of endosomal membrane occurs due to the structure of the hydrophobic part of the cationic PEI, in particular aspects. Variation of the ratio of ODN/PEI can increases the percentage and speed of DNA oligonucleotides released from ODN/PEI complexes.

(3) Entry of G-quartet ODNs into the nucleus. This is a useful aspect, because the inhibition of HIF-1α gene transcription by JG-ODNs occurs in the nucleus. After G-rich oligonucleotides are released into the cytoplasm, the ODNs form the G-quartet structure induced by the high concentration of $K^+$ ions inside cells. Our previous results have demonstrated that G-quartet ODNs released into the cytoplasm can readily penetrate the nucleus through nuclear pores (Jing et al., 2002; Ting et al., 2003; Jing et al., 2004).

The assessment of in vivo delivery is performed as follows: JG-ODNs are labeled at the 5'-end with a fluorescent tag (FITC), dissolved in $H_2O$, heated at 90° C. for 15 minutes, gradually cooled to room temperature, and mixed with PEI at a different ratio of ODN/PEI (starting at 2:1, 1:1, 1:2, 1:4, 1:6, 1:8). ODN/PEI preparations are administered to nude mice with tumor xenografts via IP injection. At least 24 hours after injection, the mice are sacrificed, and tissues and tumor xenografts are removed and frozen. To test the efficiency of intracellular delivery and determine the JG-ODNs distribution in tissues, frozen tissue samples are sectioned, prepared, and analyzed by fluorescence microscopy, at a power of 200× or 400×, for example. The microscope pictures demonstrate the intensity of JG-ODNs in tumors delivered with a designed ratio of JG-ODN/PEI. Comparing with the results obtained from different ratio of ODN/PEI, one can identify a ratio of ODN/PEI that corresponds to an optimal efficiency for in vivo delivery.

A useful ratio of ODN and nano-carrier for JG-ODNs in vivo is determined. However, if a better vehicle (e.g. a nanoparticle) for delivering JG-ODNs is identified as described above, one can repeat the studies described above using the novel identified vehicle to determine the best ratio of vehicle-ODN for JG-ODN administration in vivo. Also, one can perform in vivo drug tests by using both PEI and a novel drug carrier to determine whether the drug efficacy of JG-ODNs in vivo is promoted by the new carrier.

IV. Lipid Compositions

In certain embodiments, the present invention concerns a novel G-rich oligonucleotide composition, including one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, for example, comprising one or more lipids associated with the present invention. Exemplary lipids include Lipofectin, N-[1-(2,3-dioleyoxy)propyl-N,N, N-trimen-thylammonium chloride (DOTMA), and dioleoylphotidylethanolamine (DOPE) used as delivery vehicles. A G-rich oligonucleotide associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/G-rich oligonucleotide associated composition of the present invention is not limited to any particular structure. For example, they may also simply be interspersed in a solution, possibly forming aggregates that are not uniform in either size or shape. In another example, they may be present in a bilayer structure, as micelles, or with a "collapsed" structure. In another non-limiting example, a lipofectamine (Gibco BRL)-G-rich oligonucleotide or Superfect (Qiagen)-G-rich oligonucleotide complex is also contemplated.

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In a further embodiment, the lipid may be a charged. For example, charged phospholipids may be used for preparing a lipid composition according to the present invention and can carry a net positive charge or a net negative charge. In one embodiment, the charge lipid may be a "polycationic polymer", which as used herein is defined as a water-soluble positively charged compound. The polycationic polymer neutralizes the negative charge of the nucleic acids allowing close proximity of the nucleic acids to the negatively charge cell membrane. Exemplary polycationic polymers include but are not limited to, polylysine, polyethyleneimine, polyhistidine, protamine, polyvinylamines, polyvinylpyridine, polymethacrylates, and polyornithine. Other exemplary delivery vehicles include but are not limited to the nanopolyer, PEI.

A. Emulsions

A lipid can be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

B. Micelles

A lipid can be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al., 1973, each incorporated herein by reference). For example, one or more lipids are typically made into a suspension in an organic solvent, the solvent is evaporated, the lipid is resuspended in an aqueous medium, sonicated and then centrifuged.

V. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In particular embodiments, a lipid and/or G-rich oligonucleotides may be, for example, encapsulated in the aqueous interior of a liposome, interspersed within the lipid bilayer of a liposome, attached to a liposome via a linking molecule that is associated with both the liposome and the G-rich oligonucleotides, entrapped in a liposome, complexed with a liposome, etc.

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the G-rich oligonucleotides, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the G-rich oligonucleotide is about 0.7 to about 1.0 µm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728, 578, 4,728,575, 4,737,323, 4,533,254, 4,162,282, 4,310,505, and 4,921,706; International Applications PCT/US85/01161 and PCT/US89/05040; U.K. Patent Application GB 2193095 A; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/G-rich oligonucleotides or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

A. Liposome Targeting

Association of the G-rich oligonucleotide with a liposome can improve biodistribution and other properties of the G-rich oligonucleotide. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/G-rich oligonucleotide composition can comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of G-rich oligonucleotides. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

B. Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars.

C. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986). Liposomes containing anti-disialoganglioside GD2 monoclonal antibodies have been used to aid the targeting of the liposomes to cells expressing the tumor antigen (Pagnan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a G-rich oligonucleotide can be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific G-rich oligonucleotide delivery and/or targeting vehicle can comprise a specific binding ligand in combination with a liposome. The G-rich oligonucleotides to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a G-rich oligonucleotide-binding agent. Others comprise a cell receptor-specific ligand to which G-rich oligonucleotides to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor.

VI. Lipid Administration

The actual dosage amount of a lipid composition (e.g., a liposome-G-rich oligonucleotide) administered to an individual can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage.

VII. Treatment and/or Prevention of Cancer

In certain embodiments, cancer is treated and/or prevented by administering to a subject an effective amount of a G-rich oligonucleotide. The subject may be a mammal, such as a human, for example.

The oligonucleotides of the present invention may have any percentage of guanosine bases that allow for tetrad formation provided that the oligonucleotide exhibits anti-cancer activity.

In particular embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder, for example.

The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell. The cancer cell may comprise a cancer stem cell, in certain embodiments.

In a particular embodiment of the present invention, G-rich oligonucleotides are administered in an effective amount to decrease, reduce, inhibit or abrogate the growth of a tumor. In specific embodiments of the present invention, G-rich oligonucleotides inhibit HIF1α. The oligonucleotide may inhibit the function and/or activity and/or expression of HIF1α.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, patients to be treated will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

To kill cells, inhibit cell growth, decrease tumor or tissue size and otherwise reverse or reduce the malignant phenotype of tumor cells, using the methods and compositions of the present invention, one would generally contact a hyperproliferative cell with the G-rich oligonucleotide. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a G-rich oligonucleotide. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

In certain embodiments, the tumor being treated may not, at least initially, be resectable. Treatments with therapeutic antibodies may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

VIII. Combination Treatments

In specific embodiments in which the G-rich oligonucleotides of the present invention are employed, it may be desirable to combine the oligonucleotides of the present invention with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, and/or increasing the lifespan of a subject with cancer. Anti-cancer agents include biological agents (biotherapy), chemotherapy agents, immunotherapy agents, surgery, and radiotherapy agents. More generally, these other compositions would be provided in a combined amount effective to kill or inhibit proliferation of the cell. This process may involve contacting the cells with the antibodies of the present invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the oligonucleotides and the other includes the second agent(s).

Alternatively, the oligonucleotides of the present invention may precede or follow the other anti-cancer agent treatment by intervals ranging from minutes to weeks. In embodiments where the other anti-cancer agent and oligonucleotides are applied separately to the individual or a cell thereof, one would generally ensure that a significant period of time did not expire between the time of each delivery, such that the agent and oligonucleotides would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly, however, where several days (2, 3, 4, 5, 6 or 7, for example) to several weeks (1, 2, 3, 4, 5, 6, 7 or 8, for example) lapse between the respective administrations.

A. Chemotherapy

Cancer therapies also include a variety of chemical-based treatments. Some examples of chemotherapeutic agents include antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Taxol, Vincristine, Vinblastine, miscellaneous agents such as Cisplatin (CDDP), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine.

Some examples of other agents include, but are not limited to, Carboplatin, Procarbazine, Mechlorethamine, Camptothecin, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabien, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

B. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

D. Gene Therapy

In yet another embodiment, gene therapy in conjunction with the combination therapy using the oligonucleotides compounds described in the invention are contemplated. A variety of genes that may be targeted for gene therapy of some form in combination with the present invention include, but are not limited to growth factors, receptor tyrosine kinases, non-receptor tyrosine kinases, SER/THR protein kinases, cell surface proteins, cell signaling proteins, guanine nucleotide exchangers and binding proteins, or nuclear proteins, or nuclear transcription factors.

E. Other Agents

It is contemplated that other agents may be used in combination with the present invention to improve the therapeutic efficacy of treatment. One form of therapy for use in conjunction with chemotherapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

F. Vaccines

It is contemplated that vaccines that are used to treat cancer may be used in combination with the present invention to improve the therapeutic efficacy of the treatment. Such vaccines include peptide vaccines or dendritic cell vaccines. Peptide vaccines may include any tumor-specific antigen that is recognized by cytolytic T lymphocytes. Yet further, one skilled in the art realizes that dendritic cell vaccination comprises dendritic cells that are pulsed with a peptide or antigen and the pulsed dendritic cells are administered to the patient.

Examples of tumor-specific antigens that are being used as vaccines in melanoma include, but are not limited to gp100 or MAGE-3, for example. These antigens are being administered as peptide vaccines and/or as dendritic cell vaccines.

IX. Pharmaceutical Compositions

In certain aspects of the present invention, there are methods to treat an individual with cancer and/or prevent cancer in an individual comprising administering a therapeutically effective amount of an oligonucleotide of the invention. In such cases, the oligonucleotide may comprise a pharmaceutically acceptable carrier.

A. Pharmaceutically Acceptable Carriers

Aqueous compositions of the present invention comprise a therapeutically effective amount (used interchangably herein with the term "effective amount") of an oligonucleotide dissolved and/or dispersed in a pharmaceutically acceptable carrier and/or aqueous medium.

The phrases "pharmaceutically and/or pharmacologically acceptable" refer to molecular entities and/or compositions that do not produce an adverse, allergic and/or other untoward reaction when administered to an animal, and/or a human, as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

If biological material is employed, it should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of an oligonucleotide as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

An oligonucleotide of the present invention can be formulated in any suitable manner. The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations that are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1% 2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%.

The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

B. Lipid Formulations and/or Nanocapsules

In certain embodiments, the use of lipid formulations and/or nanocapsules is contemplated for the introduction of an oligonucleotide into host cells. Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Nanocapsules can generally entrap compounds in a stable and/or reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and/or such particles may be easily made.

In a specific embodiment of the invention, the oligonucleotide may be associated with a lipid. The oligonucleotide associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/oligonucleotide compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances that may be naturally occurring or synthetic lipids. For example, lipids include the fatty droplets that naturally occur in the cytoplasm as well as the class of compounds which are well known to those of skill in the art which contain long chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids. Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about 20° C. Preferably, chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self associate. For example, when aqueous phases are present both within and without the liposome, the lipid molecules may form a bilayer, known as a lamella, of the arrangement XY YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear shaped flask. The container should have a volume ten times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25 50 mM phospholipid in sterile, pyrogen free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287 341, the contents of which are incorporated herein by reference; the method of Deamer and Uster (1983), the contents of which are incorporated by reference; and the reverse phase evaporation method as described by Szoka and Papahadjopoulos (1978). The aforementioned methods differ in their respective abilities to entrap aqueous material and their respective aqueous space to lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50 200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

C. Dosage

The compounds (active ingredients) of this invention can be formulated and administered to treat a cancer patient, in particular an endocrine therapy-resistant cancer patient, by any means that produces contact of the active ingredient with the agent's site of action in the body of a vertebrate. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired. The active ingredient(s) of the present invention include an AIB1 antagonist and/or an endocrine therapy, such as an adjuvant.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, subcutaneously, transdermally or as a suppository. In administering a compound, the compound may be given systematically. For compounds which require avoidance of systemic effects, a preferred embodiment is intrathecal administration. In a preferred embodiment, of the invention the compound is administered interarticularly for the treatment of arthritis.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrrolidone, ethylenevinylacetate, methyl cellulose, carboxymethyl cellulose or protamine sulfate. The concentration of macromolecules as well as the methods of incorporation can be adjusted in order to control release. Additionally, the AIB1 antagonist and/or the adjuvant of the present invention can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows. Pharmacological ranges for the active ingredients can be determined by the skilled artisan using methods well known in the art. Example ranges for the antagonist of an AIB1 polypeptide and/or the adjuvant may comprise about 0.0001 to 1.0 milligrams, and/or about 0.001 to 0.1 milligrams, and/or about 0.1 to 1.0 and/or even about 10 milligrams per dose and/or so. Multiple doses may be administered. Alternatively, a single dose is administered hourly, daily, weekly or monthly of a combination thereof. Alternatively, multiple doses are administered hourly, daily, weekly or monthly or a combination thereof. Example formulations are provided below, and are not intended to be limiting or exemplary formulations of the present invention:

Capsules: Capsules are prepared by filling standard two-piece hard gelatin capsulates each with powdered active ingredient, 175 milligrams of lactose, 24 milligrams of talc and 6 milligrams magnesium stearate.

Tablets: Tablets are prepared by conventional procedures so that the dosage unit contains the indicated amount of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 milliliters contains the indicated amount of finely divided active ingredient, 200 milligrams of sodium carboxymethyl cellulose, 5 milligrams of sodium benzoate, 1.0 grams of sorbitol solution U.S.P. and 0.025 milliliters of vanillin.

Accordingly, the pharmaceutical composition of the present invention may be delivered via various routes and to various sites in an animal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

X. Kits of the Invention

The present invention includes kits that may be utilized for treatment and/or prevention of cancer. In specific embodiments, the kits and all components therein are housed in a suitable container. In particular embodiments, the kits include one or more oligonucleotides, including one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and/or a combination thereof.

In specific embodiments of the present invention, the kits and/or reagents therein are housed in one or more suitable containers. In particular aspects, the kits include additional reagents, such as pharmaceutically acceptable carriers, additional anti-cancer agents, and so forth. In other embodiments, the kit includes one or more reagents or apparatuses for obtaining a sample from an individual, such as a scalpel, forceps, syringe, tongue depressor, needle, toothpick, and so forth.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Methods and Reagents for Inhibition of HIF1α

Exemplary embodiments of methods and compositions for inhibition of HIF1α are provided herein.

Design of G-Rich Oligonucleotides as Potent HIF-1α Inhibitors

Mounting evidence demonstrated that HIF-1α is a very important molecular target for human cancer therapy. Therefore, development of HIF-1α inhibitors is a critical step of establishing a novel therapeutic strategy for human cancers. Recently, 10 novel G-rich oligodeoxynucleotides (ODN) (JG240-JG249) were designed, which form an intra-molecular quadruplex DNA structure (called as G-quartet), as inhibitors of HIF-1α and the sequences of the G-rich ODNs shown in Table 1.

TABLE 1

Inhibition of HIF-1α activation by designed G-rich oligos

| Oligos | Sequence | IC$_{50}$ (µM) |
|---|---|---|
| T40214 | GGGCGGGCGGGCGGGC (SEQ ID NO: 1) | N/A |
| T40231 | GGTGGGTGGGTGGG (SEQ ID NO: 2) | N/A |
| T40232 | GGCGGGCGGGCGGG (SEQ ID NO: 3) | N/A |
| T40233 | GGCGGGTGGGCGGG (SEQ ID NO: 4) | N/A |
| JG240 | GGTGGGCGGGTGGG (SEQ ID NO: 5) | 4.55 |
| JG241 | GGTGGGCAGGTGGG (SEQ ID NO: 6) | 2.46 |
| JG242 | GGTGGGTAGGTGGG (SEQ ID NO: 7) | 2.56 |
| JG243 | GGCGGGCAGGCGGG (SEQ ID NO: 8) | 1.56 |
| JG244 | GGCGGGTAGGCGGG (SEQ ID NO: 9) | 2.07 |
| JG246 | GGTAGGTGGGTAGG (SEQ ID NO: 10) | 2.76 |
| JG247 | GGTAGGCGGGTAGG (SEQ ID NO: 11) | N/A |
| JG248 | GGTAGGCAGGTAGG (SEQ ID NO: 12) | 4.46 |
| JG249 | GGTAGGTAGGTAGG (SEQ ID NO: 13) | 5.72 |

T40214, which is a Stat3 inhibitor (Jing et al., 2003; Jing et al., 2004; Jing et al., 2005; Jing et al., 2006), was used as a control. Also, G-rich oligonucleotides have been previously developed as inhibitors of HIV integrase (Jing et al., 1997; Jing and Hogan, 1998; Jing et al., 2000a and 2000b; Jing et al., 2002).

Figure 3:
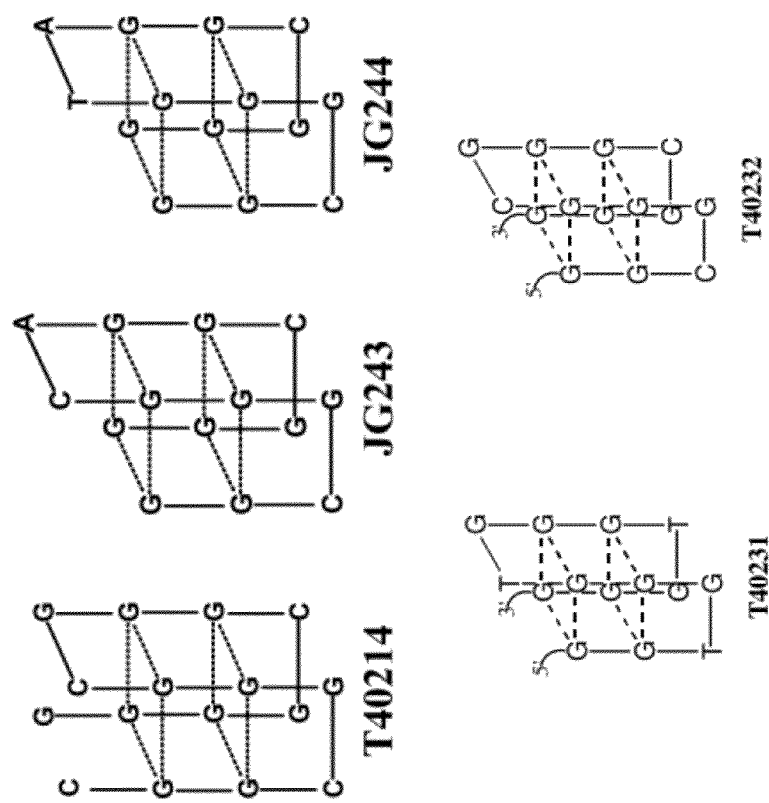
FIG. 3 shows exemplary G-quartet structures of T40214 (SEQ ID NO:1), JG243 (SEQ ID NO:8), JG244 (SEQ ID NO:9), T40231 (SEQ ID NO:2), and T40232 (SEQ ID NO:3).
Figure 4:
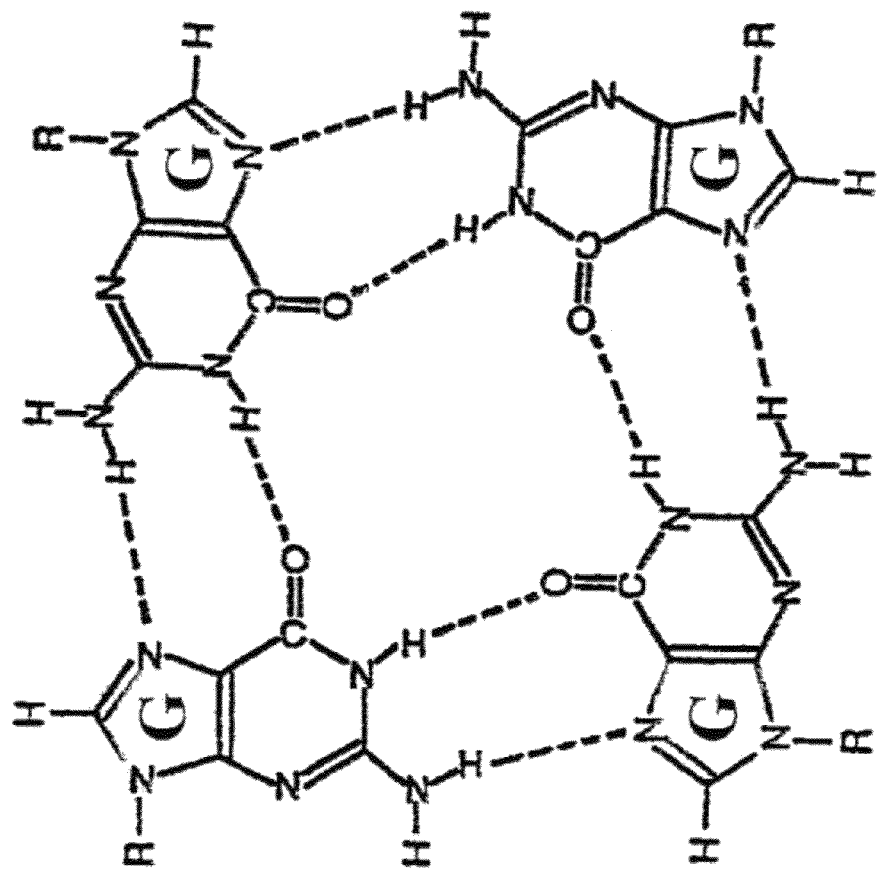
FIG. 4 provides illustration of an exemplary H-bond formation of G-quartet bases.
Figure 5:
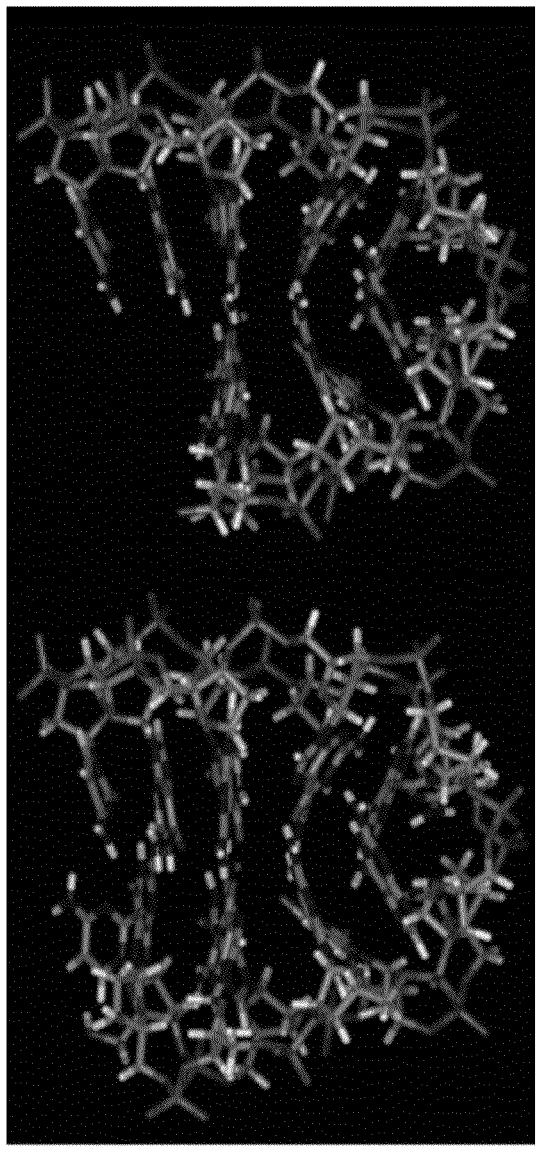
FIG. 5 demonstrates molecular structures of T40214 and JG243.
Figure 17:
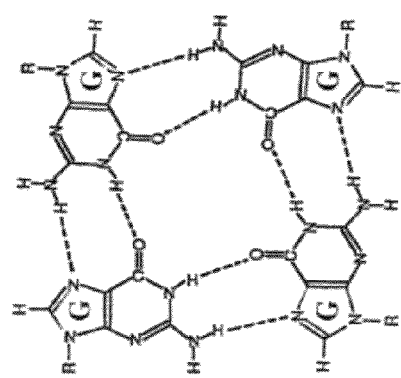
FIG. 17 illustrates an exemplary G quartet in T40231 (SEQ ID NO:2).
Figure 17:
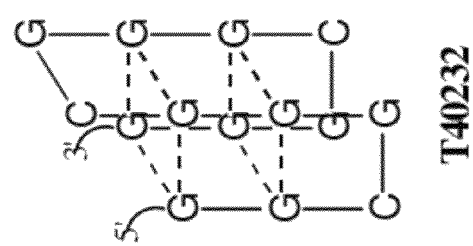

Molecular Structures of the Designed JG-ODNs (i) Structures of JG-ODNs. The designed G-rich oligos with 14 residues are expected to form intramolecular G-quartet structures, which are composed of two G-quartets in the middle with one X-Y-X-Y loop on the bottom and one Y-X loop on the top (X represents: Thymine or Cytosine; and Y represents: Adenine or Guanine) (FIGS. 3, 4, and 17). T40214 has been determined to form a G-quartet structure by NMR, CD, UV and modeling (Jing and Hogan, 1998; Jing et al., 2000). The structures of the designed JG-ODNs were determined by modification of the NMR structure of T30923, analog T40214 (Jing et al., 2000), and optimized by INSIGHTII/DISCOVER programs in a Dell computer workstation (FIG. 5). The difference between the structure of T40214 and the structures of JG-ODNs, such as JG243, is on the top loop domain of G-quartets. T40214 forms a symmetric quadruplex, similar to a cylinder. However, JG-ODNs are expected to form asymmetric chair quadruplex. The chair G-quartet structures were proved to be a key structure for JG-ODNs binding into the active site of HIF-1α to block the interaction between HIF-1α and the protein of p300/CBP.

(ii) Non-denatured DNA gel. To determine whether the designed G-rich ODN can form G-quartet structure or not, a non-denatured gel electrophoresis was run. First, the JG-ODNs labeled with $^{32}$P in 50 mM KCl solution were heated at 90° C. for 10 minutes, then cooled at 4° C. for 30 minutes. 20% nondenaturing polyacrylamide gels, containing 1×TBE, 10% AP and 30 µL TEMED, in 1×TBA buffer was pre-cooled in a 4° C. cold room for an hour. The prepared samples were run on 20% nondenaturing polyacrylamide gels in a 4° C. cold room for 6 hours.

Figure 6:
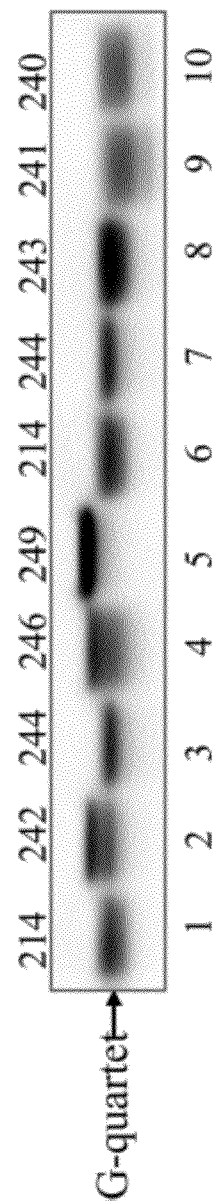
FIG. 6 shows electrophoresis of exemplary JG-ODNs.

FIG. 6 showed that the bands of JG243 and JG244 have the same migration compared with that of T40214. T40214 was used as a control since its molecular structure has been determined as an intramolecular G-quartet structure (Jing and Hogan, 1998; Jing et al., 2002). The migrational rate in non-denaturing gels depends on molecular structure of the G-quartet oligonucleotides. The same migration of JG243, JG244 and T40214 demonstrates that they form the same molecular structures with similar size. Therefore, JG243 and JG244 clearly form an intramolecular G-quartet structure. However, JG246 seems to form two different G-qauret structures, one structure is the same with JG243 or JG244 and another seems to form similar structure with JG249, which is expected to form a dimer G-quartet structure since its migrational rate is slower than that of T40214. Moreover, JG240 and JG241 form the same structure with JG244; JG242 have the same structure with JG246; and JG247 and JG248 form the same structure with JG249, respectively.

Determination of the Inhibition of HIF-1α Activation (IC50) for the Designed JG-ODNs in Human Cancer Cells (i) Western Blots. To determine the drug activity of JG-ODNs in cancer cells, the studies were performed as follows: (1) the cancer cell lines (e.g. pancreatic cancer cells PANC-1) were cultured in Dulbecco's modified Eagle's medium (Life Technologies, Inc., Grand Island, N.Y.) supplied with 10% fetal bovine serum, 100 IU/ml penicillin, and 10 ug/ml streptomycin, and maintained in 37° C. incubator with 5% $CO_2$. (2) JG-ODNs were synthesized by a chemical synthesis company, Midland Certified Reagent Co. (Midland, Tex.). JG-ODNs mixed with PEI (polyethylenimine, 25K Aldrich Chemical, Wis.) at the ratio of 4:1. PEI was used as vehicle for drug delivery. Then the mixed JG-ODN/PEI was added to the 6-well plates (about 6-9×10$^5$ cells/well) after the cells were seeded. The concentrations of JG-ODNs added in 6-well plates were: 0, 0.5, 1.0, 2.5, and 5.0 µM. After incubation for 5 hrs in the $CO_2$ incubator, cells were washed three times with fresh medium, and put into a hypoxia chamber (BioSpherix, Redfield, N.Y.) to continue incubation with 1% $O_2$, 5% $CO_2$ and 94% $N_2$ for 16 hrs before extraction. (3) Western Blot Analysis was performed to determine the drug activity.

(ii) IC$_{50}$s of HIF-1α inhibition by JG-ODNs. The results of drug activities of JG-ODNs showed in FIG. 7 and Table 2.

TABLE 2

Drug activity of JG-ODNs

| Oligos | IC$_{50}$ (µM) |
|---|---|
| T40214 | N/A |
| JG240 | 4.55 |
| JG241 | 2.46 |
| JG242 | 2.59 |
| JG243 | 1.56 |
| JG244 | 2.07 |
| JG246 | 2.76 |
| JG247 | N/A |
| JG248 | 4.46 |
| JG249 | 5.72 |

Figure 7:
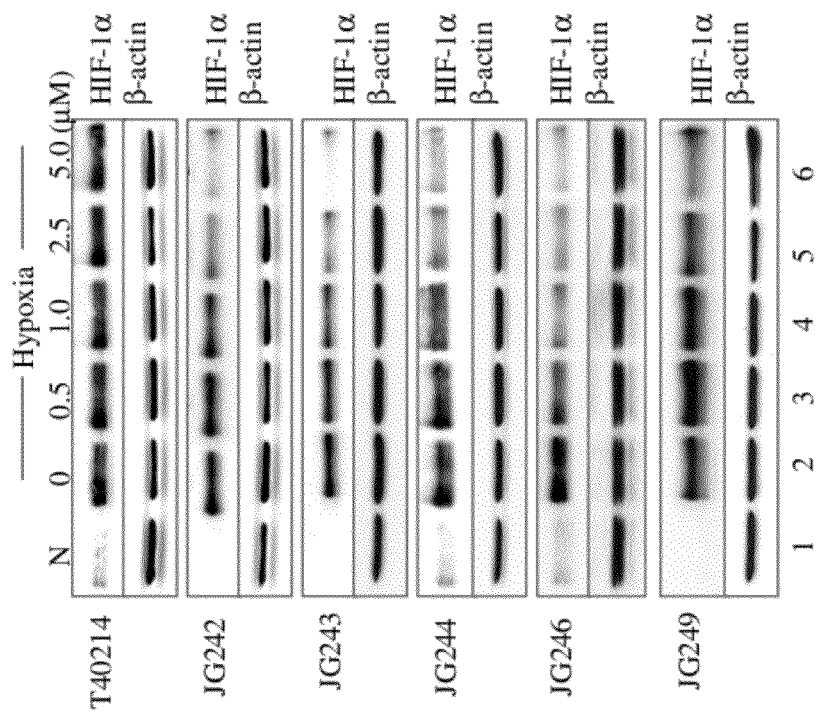
FIG. 7. provides western blots that showed the drug activity of JG-ODNs. N: normoxic conditions, HIF-1α has no activation under the condition. JG-ODNs suppress the expression of HIF-1α activation in cells under hypoxia xondition. T40214 as control ODN has no activity to HIF-1α. β-actin was used as a control for protein equal loading.

FIG. 7 shows that western blots demonstrated that in normoxic condition (Lane 1), HIF-1α has no activation since HIF-1α has a short life-time (~5 min) and then is rapidly degraded by the ubiquitin-proteasome system. However, under hypoxia condition, HIF-1α is not hydroxylated because the major substrate, dioxygen, is not available. The unmodified HIF-1α protein escapes the VHL-binding, ubiquitination, and degradation, and then dimerizes, thereby stimulating the transcription of its target genes. When $N_8O_3$ is not asparaginyl-hydroxylated, p300 and CBP can bind to HIF-1α, allowing transcriptional activation of HIF-1 target genes. Western blots showed that the designed JG-ODNs significantly inhibit the expression of HIF-1α under hypoxia condition. The $IC_{50}$s (50% inhibitory concentration) were determined by analysis of the intensities of the bands of HIF-1α in Western blots using the intensity of the band of HIF-1α without adding JG-ODNs as a control (Lane 2).

Based upon the results, it was found that nine designed JG-ODNs have strong abilities to inhibit HIF-1α activation in cancer cells under hypoxia condition and the $IC_{50}$s are less than 5 μM. JG243 and JG244 were selected to be the most active candidates for further in vivo tests since they have the best $IC_{50}$s and form an intramolecular G-quartet structures as well. It is also noted that T40214 as a control has no drug activity for inhibiting HIF-1α activation.

Mechanism of Inhibition of HIF-1α Activation by JG-ODNS

Molecular modeling and computational analysis were used to estimate the mechanism of inhibition of HIF1α activation by JG-ODNs. This approach is based upon two assumptions: (i) the NMR structure of C-terminal domain of HIF1α (Dames et al., 2002) contains a reasonable molecular shape of the binding site to p300/CBP and (ii) the complex of HIF-1α/JG-ODN obtained from molecular docking is a useful starting point for searching for an effective inhibitor.

(i) Computational studies. GRAMM programs were employed in this study (Katchalski-Katzir et al., 1992; Ritchie and Kemp, 2000). GRAMM performs an exhaustive grid-based search for surface complementarity of the receptor-ligand complex. This program is based on a geometry-based algorithm for predicting the structure of a possible complex between molecules of known structures. It can provide quantitative data related to the quality of the contact between the molecules. The intermolecular energy calculation relies on the well-established correlation and Fourier transformation techniques used in the field of pattern recognition. The docking calculation by GRAMM predicts the structure of complex formed between the two constituent molecules by using their atomic coordination, without any prior information as to their binding sites. The computational approach was carried out on a Dell computer workstation with SYBYL program.

Figure 8:
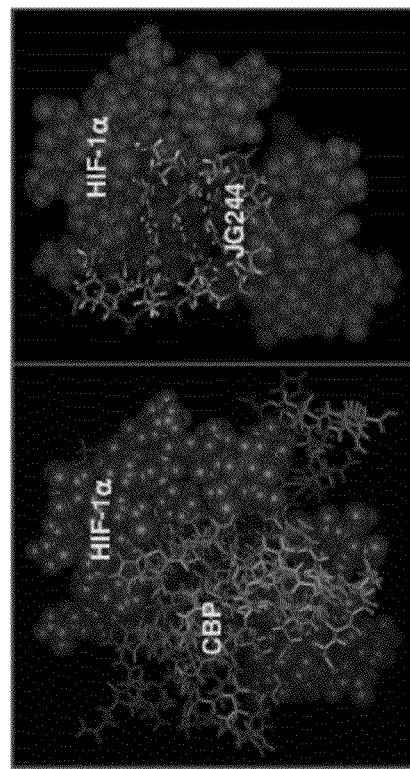
FIG. 8A demonstrates a histogram showed the distribution of H-bonds formed between JG244 and C-terminal domain of HIF-α. Based upon 1000 docking complexes, 47.8% of the H-bands distribute into the area of residue 796 to 806, which was identified as binding site for JG-ODN.
FIG. 8B shows the NMR structure of the complex: in the left panel the complexes of CBP binding into C-terminal domain of HIF1α (Dames et al., 2002) and the docking structure of the complex of JG244 binging into C-terminal domain of HIF1α (right panel). The complexes showed that JG244 blocks the binding interaction between CPB and HIF-1α, since they both have the same binding site.
Figure 8:
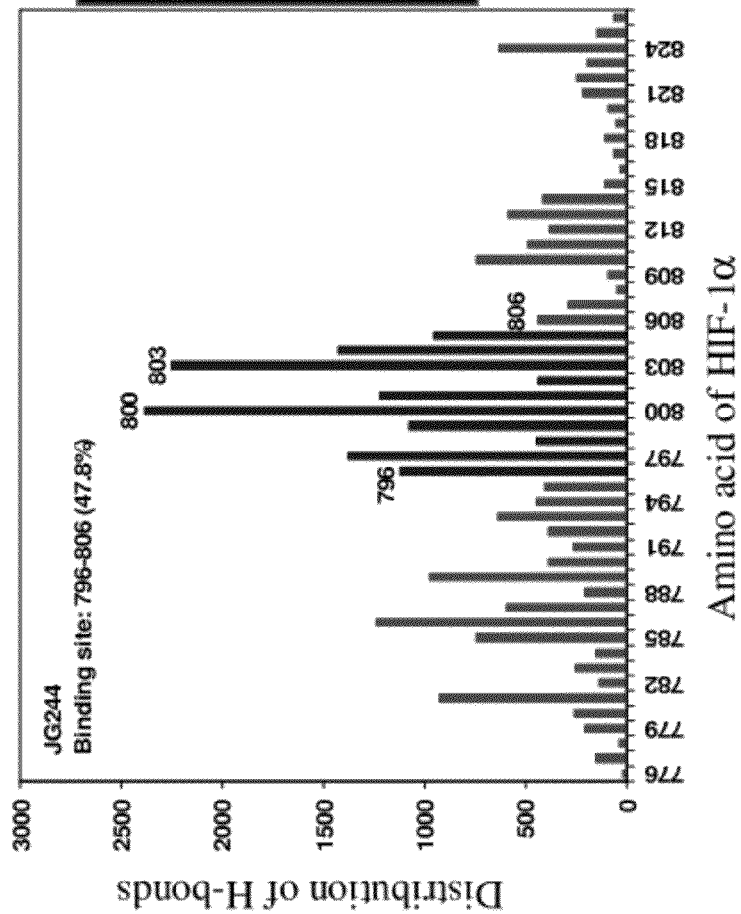

(ii) Mechanism of inhibition of HIF-1α activation by JG-ODNs. To determine the mechanism of inhibiting HIF-1α activation by JG-ODN, the inventors randomly docked JG244 1000 times onto the structures of C-terminal domain of HIF-1α, without setting any constraints, and analyzed a distribution of H-bonds formed between JG244 and C-terminal domain of HIF-1α. The histograms of H-bond distribution show that the interaction between JG244 and C-terminal domain of HIF1-α was highly concentrated on the region composed of amino acids 796 to 806 (47.8% of total H-bands)—including in the residues of $N_8O_3$ (FIG. 8).

The computational results demonstrated that 47.8% of total H-bonds formed between JG244 and HIF-1α were distributed in the region of amino acids 796 to 806, indicating that JG-ODNs strongly interact with HIF-1α by bound into the site composed of residues 796 to 806. In hypoxia, $N_8O_3$ is not asparaginyl-hydroxylated, p300 and CBP can bind to HIF-1α, allowing transcriptional activation of HIF-1 target genes. The activation of HIF-1α is involved in many cell processes, such as angiogenesis, anti-apoptosis, metabolism, metastasis, and others. Combining the results of Western blots and molecular docking, JG-ODNs significantly inhibit the activation of HIF-1α in hypoxia conditions since JG-ODNs strongly bind into the site of residues 796 to 806 of HIF-1α and block the interaction between p300/CBP and $N_8O_3$ of HIF-1α in hypoxia (FIG. 8). Therefore, JG-ODNs are potent inhibitors of HIF-1α.

JG-ODNs Reduce Angiogenesis in Cancer Cells

HIF-1 acts as master regulator of oxygen-regulated gene expression. More than 60 putative HIF-1 target genes have been identified (Semenza, 2003). Vascular endothelial cell growth factor (VEGF) is one of the major target genes and a key angiogenic factor. VEGF directly participates in angiogenesis, which specifically recruits endothelial cells into hypoxic and avascular area and stimulates their proliferation (Harris, 2002; Bicknell and Harris, 2004). Hypoxia is a stimulus of angiogenesis through the up-regulation of the VEGF expression. Suppression of the expression of VEGF is an important factor to reduce angiogenesis in hypoxia.

Figure 9:
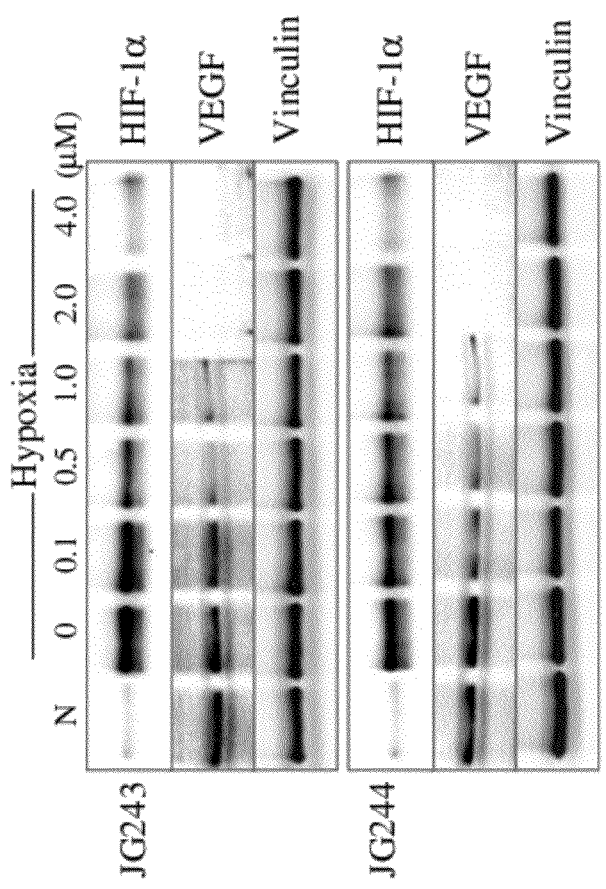
FIG. 9 shows that JG243 and JG244 block the expression of HIF1α and its downstream protein, VEGF. Vinculin is a control for equal protein loading.

The experiments were performed as described elsewhere herein. The western blots were analyzed to demonstrate the expression levels of HIF-1α and its down-stream protein, VEGF, under hypoxia. The results (FIG. 9) showed that under hypoxia the protein expressions of HIF-1α and VEGF were greatly decreased when concentration of JG-ODNs increased. The expression of VEGF was totally blocked when the JG-ODN concentration was over 2 μM. Clearly, JG243 and JG244 inhibit the activation of HIF-1α and its down-stream protein, VEGF, and significantly reduce angiogenesis in cancers. Furthermore, in similar assays it is shown that JG243 and JG244 inhibit HIF-2α. However, the expression of p53 was not disrupted by the JG-ODNs. Therefore, the results show that HIF-1α is a main HIF protein activated in pancreatic cancer cells under hypoxia and that JG-ODNs selectively inhibit HIF-1α activation and block its transcriptional protein activation.

JG-ODNs Greatly Increase Apoptosis of Human Cancer Cells

HIF-1 plays crucial roles in tumor promotion by up-regulating its target genes, which are involved in metabolism, angiogenesis, cell survival, cell invasion, and drug resistance (Hirota and Semenza, 1996; Gatenby et al., 1988).

Inhibition of HIF-1α activation not only reduces angiogenesis but also induce apoptosis leading to tumor cell death, a desirable outcome in cancer treatment.

Figure 10:
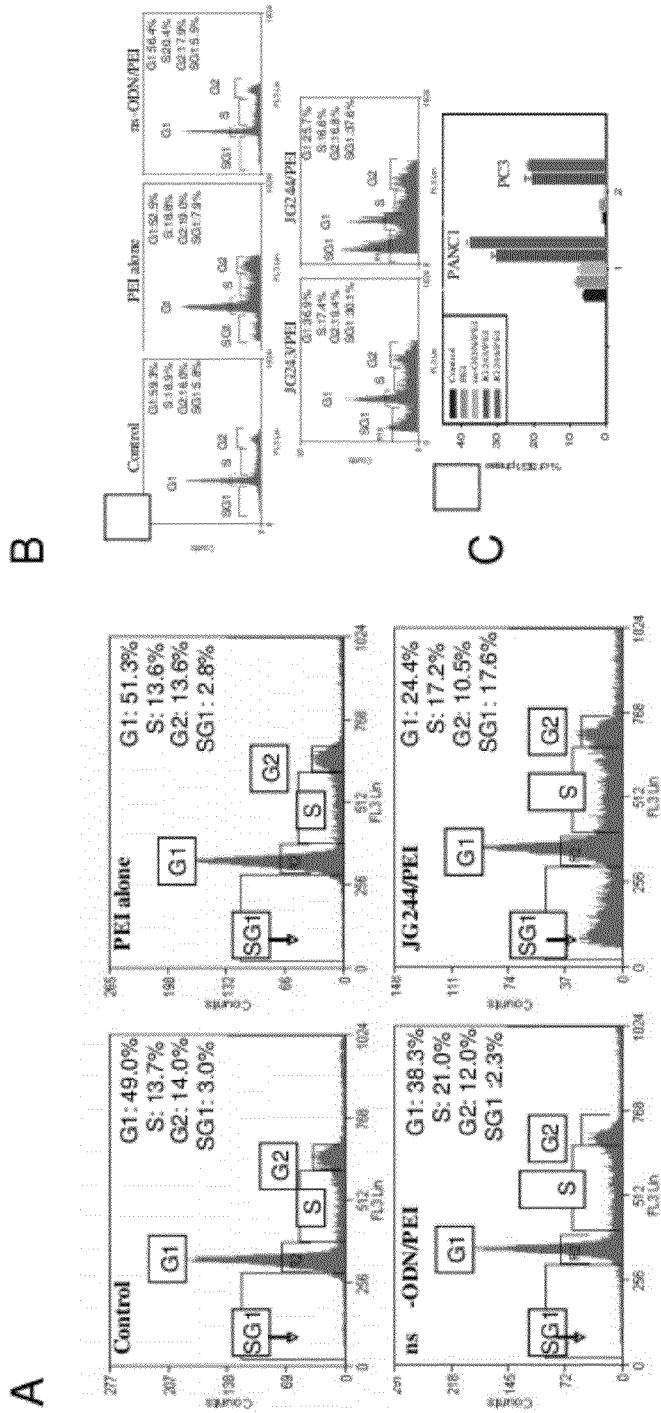
FIG. 10A showed the untreated cells; cells treated with PEI (vehicle), no-specific GQ-ODN/PEI; and JG 244/PEI.
In FIGS. 10B and 10C, the cell cycle results showed that JG243 and JG244 greatly induced apoptosis in pancreatic (PANC1) and prostate (PC3) cancer cells since SG1 corresponds to the damaged DNA in nuclei. (10B): histograms of cell cycles in PANC1 and (10C): the plot of % of SG1 for each treatment.

Flow cytometric analysis was employed to demonstrate the apoptosis in cycling cells. Briefly, pancreatic cancer cells (1 million) were fixed in 5 ml cold 80% (v/v) ethanol at 4° C. overnight. The cells were then centrifuged, washed with 1 ml PBS and resuspended in 1 ml PBS. DNase-free RNase was added and then 100 μl PI (propidium iodide; 50 μg/ml) was added. The resuspended cells were incubated in the dark at 37° C. for 1 h and covered until used. The fluorescence of the cells was measured using $10\times10^4$ cells in a FACSCalibur flow cytometer (Becton Dickinson, San Jose, Calif., USA). The fraction of cells in each cell cycle stage or undergoing apoptosis was estimated from the cellular DNA content. The results showed in the histogram of cell cycle distribution in cancer cells (MIA PANC-2) as determined with propidium iodide (PI)/flow cytometry (FIG. 10A). SG1 phase corresponds to the damaged DNA in nuclei, which results in cell death. Cell cycle results showed that the cells treated by JG244/PEI increased SG1 from 3% (treated PEI alone) to 18% of total cells, corresponding to a significant increase in apoptosis in human cancer cells.

In FIG. 10B, Here we employed flow cytometric analysis to demonstrate the apoptosis in cell cycles. Briefly, pancreatic (and prostate) cancer cells (1 million) were fixed in 5 ml cold 80% (v/v) ethanol at 4° C. overnight. The cells were then centrifuged, washed with 1 ml PBS and resuspended in 1 ml PBS. DNase-free RNase was added and then 100 μl PI (propidium iodide; 50 μg/ml) was added. The resuspended cells were incubated in the dark at 37° C. for 1 h and covered until used. The fluorescence of the cells was measured using $10 \times 10^4$ cells in a FACSCalibur flow cytometer (Becton Dickinson, San Jose, Calif., USA). The fraction of cells in each cell cycle stage or undergoing apoptosis was estimated from the cellular DNA content. The results showed in the histogram of cell cycle distribution in cancer cells (PANC1 and PC3) as determined with propidium iodide (PI)/flow cytometry. Sub-G1 (SG1) phase corresponds to the damaged DNA in nuclei, which results in cell death. The histograms demonstrated (FIG. 10C) that comparing with untreated cancer cells (control), the percentage of SG1 in cancer cells was not changed with PEI (0.5 μM) or ns-ODN/PEI (1 μM+0.5 μM) treatment, indicating that PEI as drug carrier and ns-ODN as control ODN did not induce any apoptosis in the cells. However, the SG1 of PANC1 cells treated by JG243/PEI and JG-244/PEI (1 μM+0.5 μM)) increased from 5.8% to 30.1% and 37.6%, respectively; and that of PC3 cells treated by JG243 and JG-244 increased from 0.8% to 20.4% and 21.2%, respectively. Therefore, JG-ODNs significantly promote apoptosis in cancer cells.

Drug Efficacy of JG-ODNs for Cancer Therapy

Drug efficacy of JG-ODNs for cancer therapy is established.

(i) Establishing animal xenografts with human cancers. Drug efficacy is a critical factor for novel designed anti-cancer drugs. Here, in vivo drug tests were employed for JG-ODNs in xenograft models with human cancers. In brief, the human cancer cell suspensions (e.g. prostate cancer PC3 and pancreatic cancer PANC-1) were prepared for subcutaneous injection by treating the cells with 0.25% Trypsin-EDTA for 5 minutes, followed by centrifugation of the harvested cells at 2000 rpm at room temperature for 5 minutes. The resultant cell pellets were re-suspended in 2 mL of PBS, and cell numbers counted. Two hundred microliters of tumor cell suspension (approximately $5 \times 10^6$ cells) were subcutaneously injected into each athymic nude mouse (Balb/nu/nu, 28 days old and ~20 g weight), which were obtained from NCI-Charles River Labs (Frederick, Md.). The mice injected with prostate cancer or pancreatic cancer cells have been monitored every day for tumor growth, and the tests were performed when the tumor size reached 10-50 mm$^3$.

Figure 11:
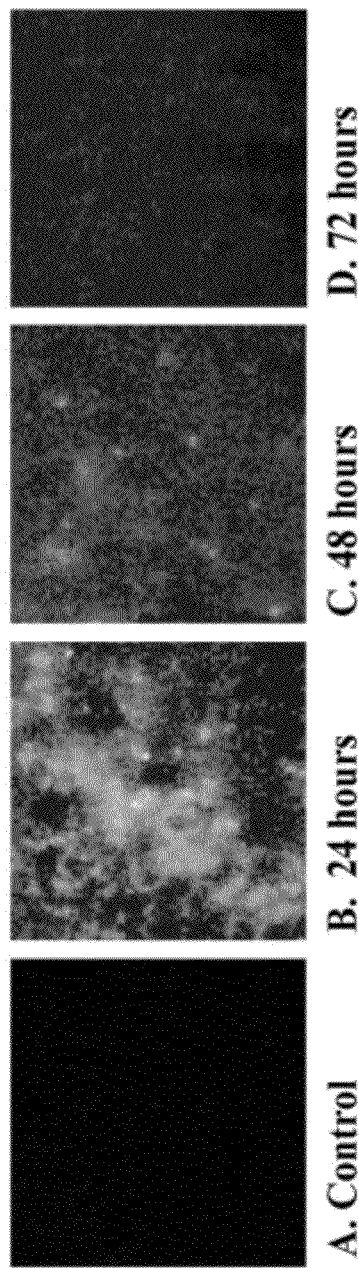
FIGS. 11A-11D provide fluorescent micrographs that show the distribution of labeled G-quartet ODN in head and neck tumors of nude mice after 24 (B), 48 (C), and 72 (D) hours. The control panel (A) indicates the tumor without drug injection (Jing et al. Mol. Can. Ther. 5:279 (2006).

(ii). Delivery of JG-ODNs into tumors of nude mice. Effective delivery of JG-ODNs into tumors of nude mice is a key to the successful cancer therapy. A novel delivery system for G-quartet ODN was established (Jing et al., 2002) (Jing et al, U.S. Pat. No. 7,119,078), which significantly increases the drug activity in cell and in vivo. In the present invention, human tumor xenografts grown in nude mice were used to determine the amount of G-quartet ODN delivered within the tumors of nude mice. First, via intra-peritoneal (IP) injection 5'-fluorescent labeled G-quartet ODN (10 mg/kg) was administered, plus PEI (2.5 mg/kg) as an intracellular vehicle. After these injections, the tumors were harvested at 24, 48, and 72 hours, and observed the tumors under fluorescent microscopy. At 48 and 72 hours, the level of G-quartet ODN in tumors was roughly 60% and 20%, respectively, of that at 24 hours (FIG. 11). The results clearly show that JG-ODN is effectively delivered within the tumors and JG-ODN structural configuration prolongs drug function in tumors, thereby, showing use as a treatment for at least pancreatic cancers, for example. This also indicates that the DNA delivery system is successful in vivo, in specific embodiments.

(iii) Determination of the drug activity of JG-ODNs in vivo. The anti-tumor activities of JG-ODNs (JG243 and JG244) were determined by following steps. Athymic nude mice with established tumors were randomly assigned to test and control groups, (4-5 mice per group) and anti-tumor activity tests were simultaneously performed in the groups: (i) a placebo group treated by PEI alone (2.5 mg/kg), which was used to be a vehicle for drug delivery; (ii) two drug test groups treated by JG243/PEI (10 mg/kg+2.5 mg/kg) and JG244/PEI (10 mg/kg+2.5 mg/kg), respectively. The nude mice with the tumor xenografts were treated via intraperitoneal (IP) injection. Each dose was injected every other day in 2-3 weeks. The period of drug treatment was generally determined based upon the rate of tumor growth and tumor effects on mice health in the placebo-treated group.

Figure 12:
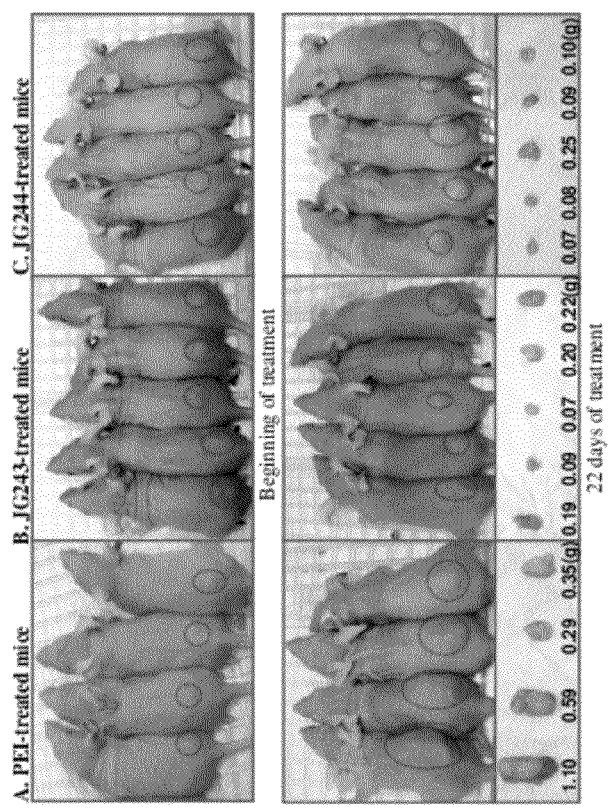
FIGS. 12A-12C demonstrate prostate tumors treated by PEI (placebo), JG243 and JG244, respectively, in 22 days. Comparing the tumor growth in placebo group, the exemplary JG243 and JG244 significantly suppress prostate tumor growth in xenograft models.
Figure 13:
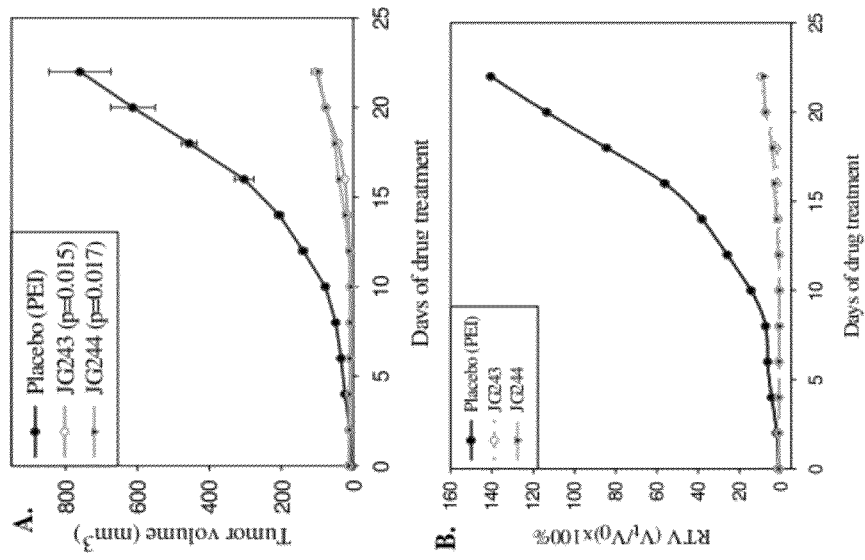
FIGS. 13A-13B show plot of tumor volumes vs. days of drug treatment (13A) and plot of RTV vs. days of drug treatment (13B).

(iv) In vivo drug activities for prostate cancer. Over the 22-day period, the mean size of prostate tumors in the PEI-treated mice increased from 5.4 to 759.5 (mm$^3$) and the mean size of prostate tumors in the mice treated with JG243 and JG244 only increased from 11.3 to 103.0 (mm$^3$) and from 12.4 to 97.6 (mm$^3$), respectively (FIGS. 12 and 13A). The plot of individual relative tumor volume (RTV) versus days of drug treatment (FIG. 13B) showed that by comparison with the tumors treated by PEI, the tumor growth rates were significantly suppressed by JG-ODN treatments. The RTV was calculated as following: $RTV=V_t/V_0$, where $V_t$ is the volume on each day of measurement and $V_0$ is the volume on the day of initial treatment. Also, it was found that the mean tumor weight of PEI-treated mice is 0.58±0.16 g and that of JG243- and JG244-treated mice are 0.15±0.07 g and 0.12±0.03 g, respectively, showing that JG-ODNs significantly suppress prostate tumor growth. The results demonstrate that the designed JG-ODNs as anti-cancer agents, e.g. JG243 and JG244, have a potent efficacy for prostate cancer.

Figure 14:
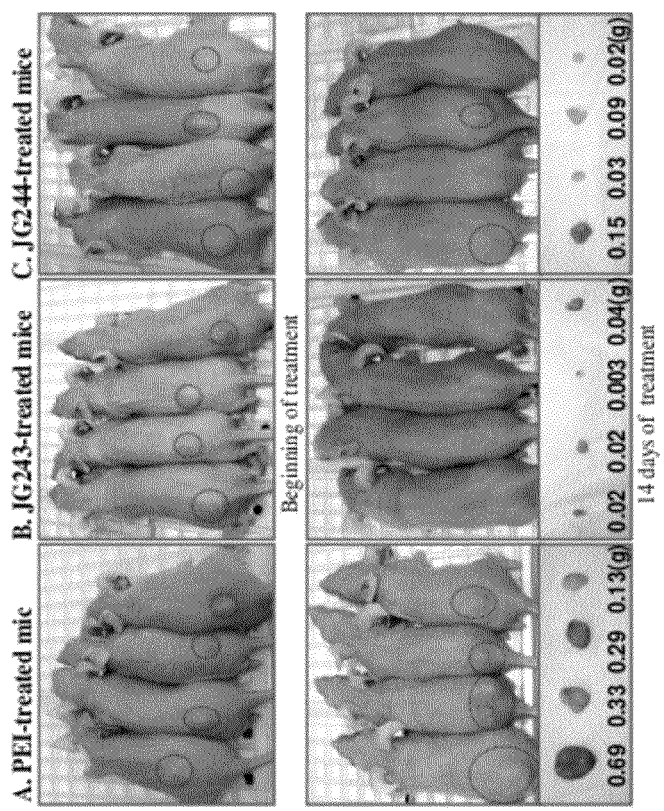
FIGS. 14A-14C show pancreatic cancer tumors treated by PEI (placebo), JG243 and JG244, respectively, in 14 days. Comparing the tumor growth in placebo group, JG243 and JG244 significantly suppress pancreatic tumor growth in xenograft models.
Figure 15:
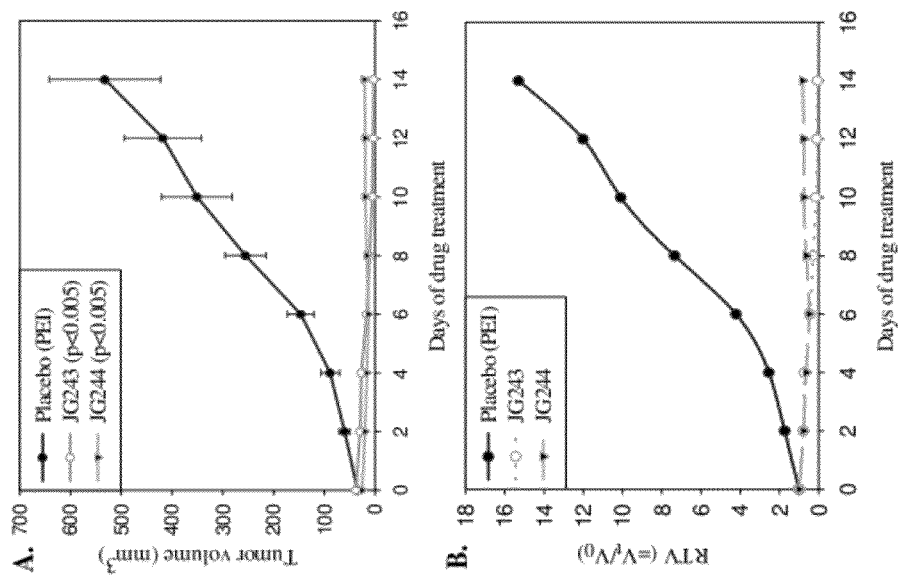
FIGS. 15A-15B show plot of tumor volumes vs. days of drug treatment in PANC-1 (15A) and plot of RTV vs. days of drug treatment in PANC-1 (FIG. 15B).

(v) In vivo drug activities for pancreatic cancer. Over a 14-day period, the mean size of pancreatic tumors (PANC-1) in PEI-treated mice increased from 34.8 to 532.1 (mm$^3$). The mean size of pancreatic tumors in the mice treated with JG243 and JG244 decreased from 37.7 to 2.4 (mm$^3$) and from 25.6 to 21.0 (mm$^3$), respectively (FIGS. 14 and 15A). The plot of RTV versus days of drug treatment (FIG. 15B) showed that the JG-ODNs induced a negative rate for pancreatic tumor growth and the tumors could no longer be detected after the two-week treatment period. Also, some PEI-treated tumors were grown as xenografts inside mice bodies and the mean tumor weight in the PEI-treated mice is 0.36±0.10 g. The mean tumor weights of JG243- and JG244-treated mice were only 0.02±0.007 g and 0.07±0.03 g, respectively. The in vivo results demonstrated that JG243 and JG244 are potentially powerful anti-cancer drugs to suppress pancreatic cancer tumors for human cancer therapy, especially for JG243, for which tumors were undetectable in all four mice during the two-week treatment.

(vi) Summary of drug activity. Summary of the in vivo drug tests are shown in Table 3. In these studies, the data demonstrate that both JG243 and JG244 are powerful anti-cancer agents that suppressed the tumor growths in nude mice and that JG-ODNs are a promising new class of anti-cancer drugs for human cancer therapy, including prostate, pancreatic, and other cancers. Drug efficacy of JG243 is the same with that of JG244 in prostate cancer therapy, but is better than that of JG244 in pancreatic cancer therapy. The mechanism of suppressing tumors for JG-ODNs was suggested that JG-ODNs inhibit the activation of HIF1α and its targeted protein, VEGF. Thus, JG-ODNs reduce angiogenesis and increase apoptosis in tumors, so significantly suppress tumor growths.

TABLE 3

Summary of in vivo drug tests for JG243 and JG244 in prostate (PC-3) and pancreatic cancer (PANC-1).

| Cancer | Group | Drug dose | # of mice | | Weight of mice (g) | | Tumor (mm³) | | Weight of tumors (g) | P value |
|---|---|---|---|---|---|---|---|---|---|---|
| | | | Start | End | Start | End | Start | End | | |
| PC-3 | Placebo (PEI) | 2.5 mg/kg | 4 | 4 | 18.8 ± 0.3 | 19.5 ± 0.8 | 5.4 ± 0.5 | 796 ± 86 | 0.58 ± 0.16 | |
| | JG243/PEI | 10 mg/kg + 2.5 mg/kg | 5 | 5 | 19.7 ± 0.3 | 20.8 ± 0.6 | 11.3 ± 2.8 | 103 ± 15 | 0.15 ± 0.07 | <0.02 |
| | JG244/PEI | 10 mg/kg + 2.5 mg/kg | 5 | 5 | 18.5 ± 0.4 | 19.4 ± 0.7 | 12.4 ± 1.6 | 98 ± 8.9 | 0.12 ± 0.03 | <0.02 |
| PANC-1 | Placebo (PEI) | 2.5 mg/kg | 4 | 4 | 20.5 ± 0.4 | 20.5 ± 0.5 | 34.8 ± 6.5 | 532 ± 110 | 0.36 ± 0.10 | |
| | JG243/PEI | 10 mg/kg + 2.5 mg/kg | 4 | 4 | 20.2 ± 0.5 | 20.9 ± 0.4 | 37.7 ± 5.4 | 2.4 ± 0.6 | 0.02 ± 0.007 | <0.005 |
| | JG244/PEI | 10 mg/kg + 2.5 mg/kg | 4 | 4 | 21.3 ± 03 | 22.1 ± 0.2 | 25.6 ± 3.5 | 21 ± 7.0 | 0.07 ± 0.03 | <0.005 |

Example 2

Lung Cancer Embodiments

In this specific embodiment, the exemplary JG244 strongly suppressed the growth of non-small cell lung cancer (NSCLC) tumor xenograft.

Lung cancer is one of the most prevalent cancers, and it is the leading cause of cancer mortality throughout the world. The majority of lung cancers are NSCLC. In 2004 alone, 1,500,000 cases of lung cancer were diagnosed. In the United States, approximately 170,000 people are diagnosed with lung cancer each year and, of those who are diagnosed, roughly 85% die of the disease; annually, the number of deaths caused by lung cancer exceeds the combined number of deaths due to breast, prostate, and colon cancers.

Figure 18:
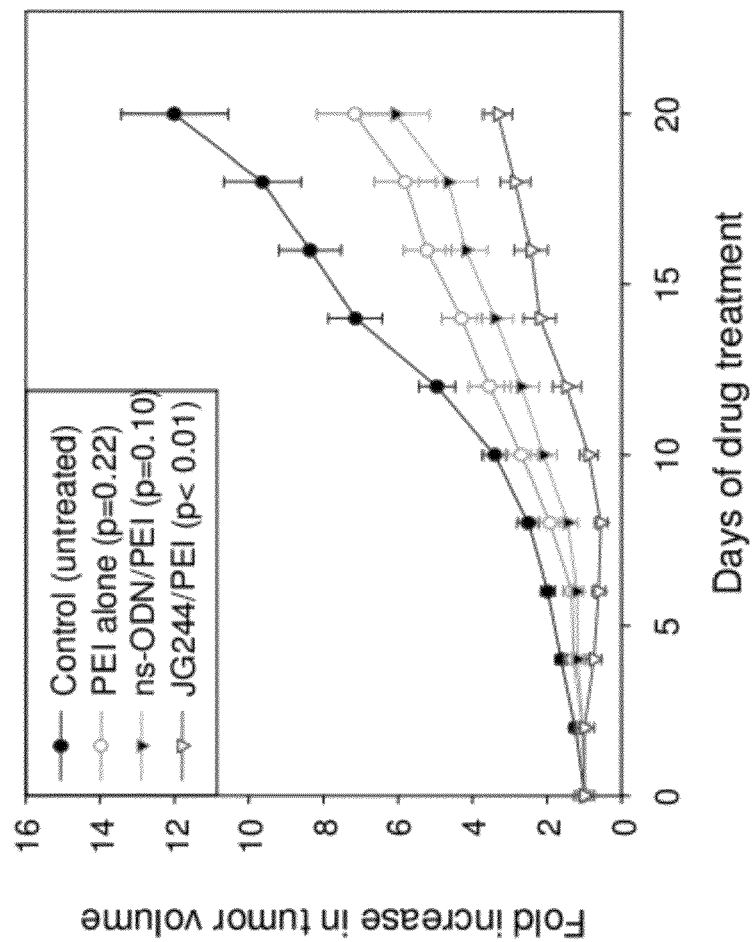
FIG. 18 shows a plot of fold increase in tumor volume vs. days of drug treatment in nude mice with NSCLC tumor (A549).
Figure 19:
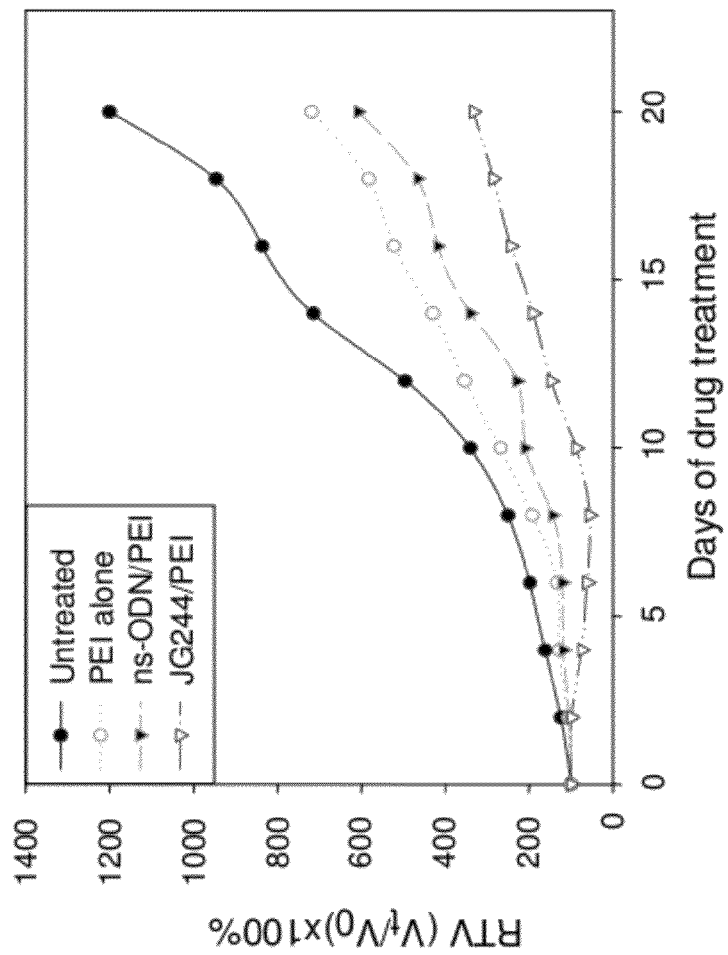
FIG. 19 provides a plot of individual relative tumor volume (RTV) vs. days of drug treatment in nude mice with NSCLC tumor (A549).

In these studies, pre-established NSCLC tumor xenografts grown in nude mice were treated with JG244 the tumor mean volume was at a start point of 226.2 (mm³). In a three-week period of drug treatment, the mean volumes of control (untreated) tumors and PEI-treated tumors increased 12-fold and 7.2-fold, respectively; and the mean volume of control ODN (non-specific ODN)-treated tumors also increased 6.1-fold; however, the mean volume of JG244-treated tumors only increased 3.3-fold (Table 4 and FIGS. 18 and 19).

inhibitor of HIF-1α activity. An exemplary SAR was based on the two critical studies: (1) the active site of HIF-1α targeted by JG-ODNs has been located; and (2) $IC_{50}$s of the inhibition of HIF-1α activation for JG-ODNs have been determined (Table 5). Then each designed JG-ODN (JG240 to JG249) were docked in the active site of HIF-1α and the binding energy was calculated between JG-ODN and HIF-1α. The binding energy was calculated by DOCK module in SYBYL7.3. (i) 3D structures of JG-ODNs were constructed and HIF-1α was downloaded from Protein Data Bank. (ii) The rational binding model for complex JG-ODN/HIF-1α was obtained by using GRAMM and HEX docking technology. The calculation was performed using Tripos force field with Gasteiger-Huckel charge and distance dependent dielectric function. (iii) The binding energy was calculated by subtracting the energy of free HIF-1α and JG-ODN from the energy of complex ($E_{bind}=E_{com}-E_{HIF}-E_{ODN}$) and the results was listed in Table 5.

Figure 20:
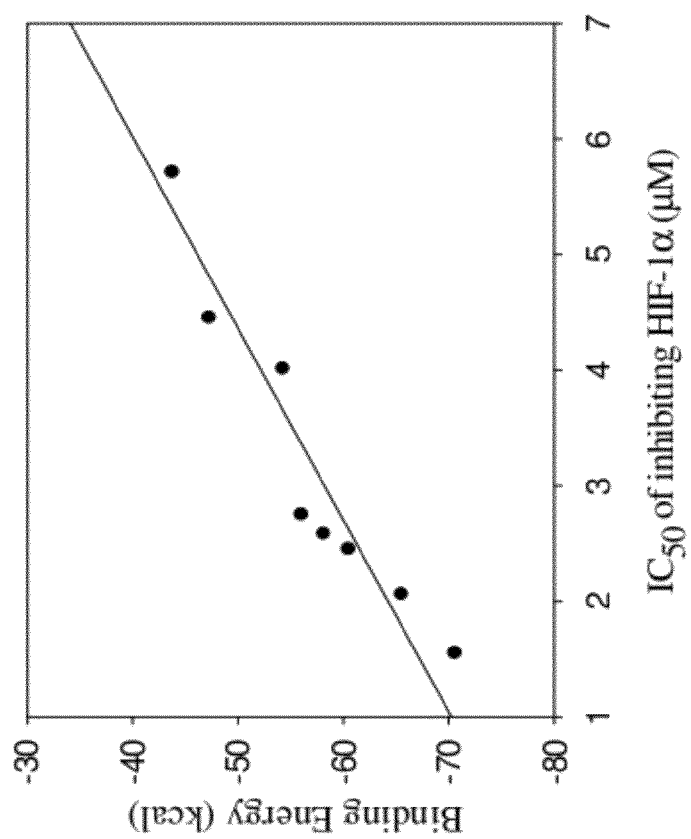
FIG. 20 shows an exemplary plot of binding energy with HIF-1α (kcarl) vs. IC$_{50}$ (μM) of inhibiting HIF-1α activation for JG-ODNs.

Linear regression analysis indicated there is a linear SAR between $IC_{50}$ and the binding energy ($R^2=0.91$) (FIG. 20). The linear relation indicates that JG-ODN with a lower binding energy corresponds to a higher drug activity. This quantitative SAR is useful for optimizing and prediction of the activity of new JG-ODNs. For example, when another JG-ODN is designed, one can first calculate its binding energy,

TABLE 4

The results of drug treated NSCLC tumors

| Cancer | Group | Drug dose | # of mice | | Weight of mice (g) | | Tumor (mm³) | | Mean Weight of tumors (g) | P value |
|---|---|---|---|---|---|---|---|---|---|---|
| | | | Start | End | Start | End | Start | End | | |
| A549 | Control | untreated | 5 | 5 | 22.7 ± 0.7 | 26.2 ± 1.2 | 91.9 ± 15 | 1103 ± 179 | 0.74 ± 0.12 | |
| | Placebo (PEI) | 2.5 mg/kg | 5 | 5 | 24.8 ± 0.9 | 28.0 ± 1.2 | 152.1 ± 28 | 1092 ± 182 | 0.60 ± 0.11 | =0.22 |
| | ns-ODN/PEI | 10 mg/kg + 2.5 mg/kg | 5 | 5 | 24.8 ± 0.7 | 29.5 ± 0.8 | 156.0 ± 26 | 947 ± 189 | 0.70 ± 0.13 | =0.10 |
| | JG244/PEI | 10 mg/kg + 2.5 mg/kg | 5 | 5 | 24.1 ± 0.7 | 27.9 ± 0.8 | 226.2 ± 58 | 750 ± 88 | 0.50 ± 0.04 | <0.01 |

The p value between untreated and JG244-treated tumors is less than 0.01 and that between PEI-treated and JG244-treated tumors is less than 0.03, showing a significant drug efficacy. Therefore, JG-ODNs as potent anti-cancer agents not only significantly suppress tumor growth of pancreatic and prostate cancers (see above) but also strongly retard the growth of NSCLC tumors in nude mice xenografts.

Example 3

Structure-Activity Relationship (SAR) Established for Novel Drug Design

A structure-activity relationship (SAR) is useful for rational drug design and is also useful for designing a potent then estimate its $IC_{50}$ based upon the SAR and determine whether the new drug is useful for use in vitro and in vivo. This established SAR assists in identifying and optimizing a novel potent anti-cancer agent.

Example 4

Additional exemplary methods and reagents for inhibition of HIF1α

Additional exemplary embodiments of methods for inhibition of HIF-1α are provided herein.

Drug Delivery System for JG243 and JG244

Figure 21:
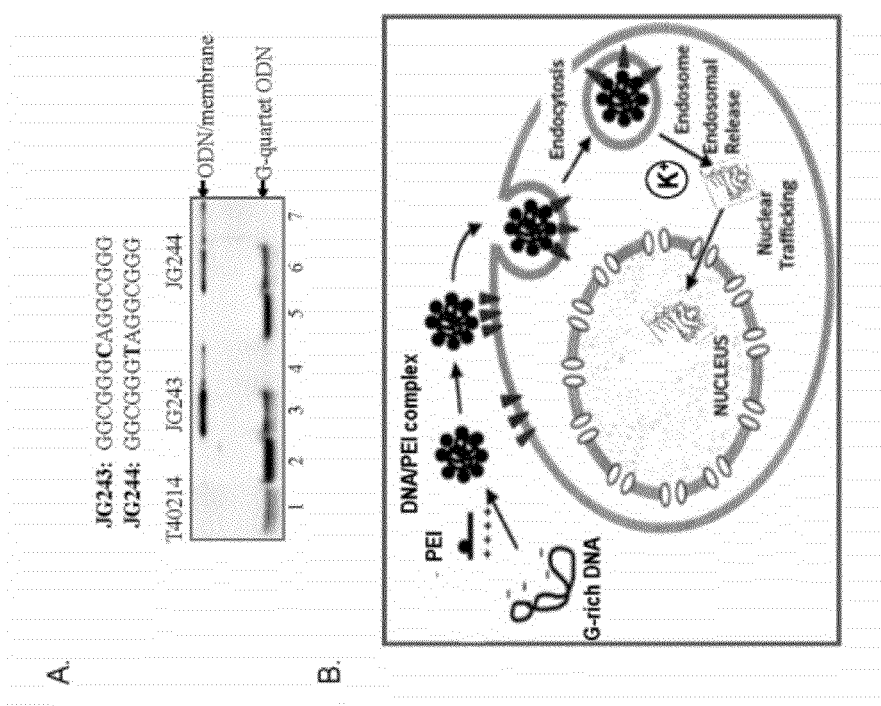
FIGS. 21A-21B show the drug delivery system for exemplary oligonucleotides JG243 (SEQ ID NO:8) and JG244 (SEQ ID NO:9).

To determine whether JG-ODNs can be delivered into cells, the following experiments were performed: $^{32}$P-labeled JG-ODNs, with or without PEI, were added to wells containing $5\times10^5$ cancer cells (FIG. 21A). After incubation for 3 hours, the wells were washed 3 times with fresh media and then the cells were maintained in culture for 24 hrs before lysed. After lysis and centrifugation, the supernatants were loaded onto a non-denaturing polyacrylamide gel. The results show that the free T40214 (Lane 1) corresponds to a G-quartet structure. With the same migrations of free T40214, free JG243 and JG244 (Lanes 2 and 5, respectively) correspond to a G-quartet structure. JG243 and JG244 with PEI (Lanes 3 and 6, respectively) has two bands, indicating that a portion of ODNs adhere on the cell membranes (the higher band) and a portion of ODNs enter into the cells (the lower band). Compared with the bands of free ODNs, the lower bands demonstrate that the ODNs inside cells form the G-quartet structures. The analysis indicated that the ratios of delivery of JG243 and JG244 are about 55% to 67%. JG243 and JG244 without PEI (Lanes 3 and 7, respectively) only showed one higher band, showing that G-rich ODN could not directly penetrate into the cells.

An effective delivery system using PEI as vehicle for JG-ODNs was established with two main steps: (i) G-rich oligos with G-quartet structure barely incorporate into cationic vehicles (FIG. 21B). Electrostatic interactions are the primary driving force responsible for forming the JG-ODN/vehicle complexes. Thus, the G-rich oligos need to be heated and denatured into random coils in order for them to incorporate with the vehicle. The JG-ODN/PEI complex was formed by mixing the denatured JG-ODN possessing negative charges with PEI, which is positively charger. The positive charges in the surface of the JG-ODN/PEI complexes enhance their cellular uptake. (ii) G-quartet formation strongly depends on the presence of cations, especially potassium. Generally, the potassium concentration is 4 mM outside cells and 140 mM inside cells. JG-ODN molecules maintain their unfolded structure before entering cells. Once delivered into cells, JG-ODN forms a G-quartet structure inside cells at high $K^+$ concentration, and then it is able to penetrate into the nucleus through nuclear pores. PEI facilitates the delivery of T40214 to target cells for endocytosis, but PEI itself cannot enter into cells due to its positive surface charges.

Structure of JG-ODNs and H-NMR Spectrum of JG244

Figure 22:
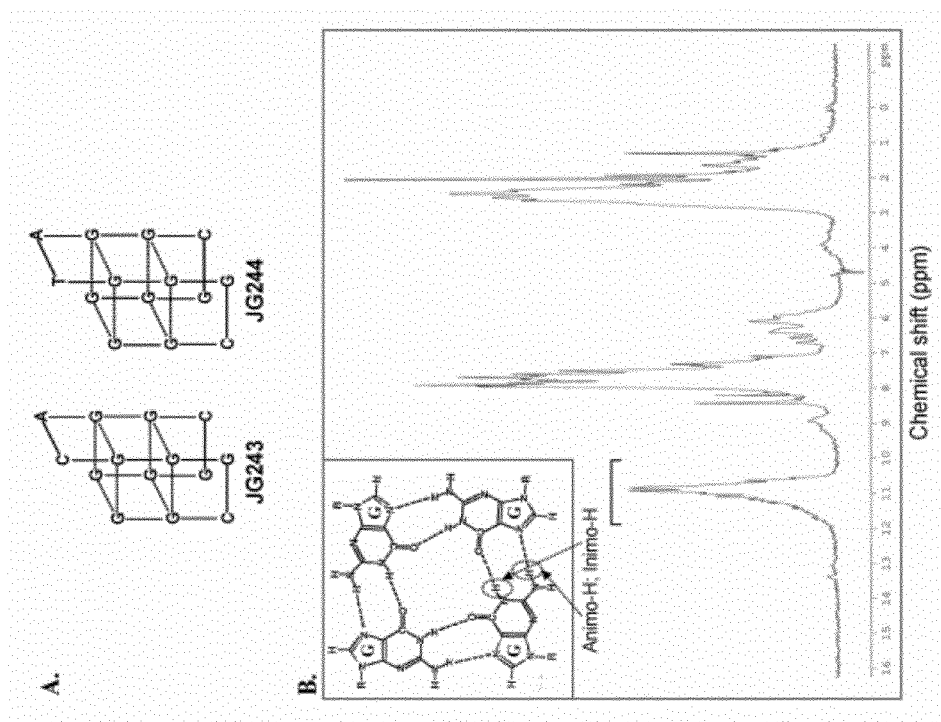
FIGS. 22A-22B show the structure of JG-ODNs and H-NMR spectrum of JG244 (SEQ ID NO:9).

FIG. 22A shows schemes of the G quartet structures of exemplary JG 243 and JG244, and FIG. 22B shows the ID proton NMR spectrum of JG244. The ID proton NMR spectrum of JG244 was obtained in 30 mM KCl at pH 7.0 and 25° C. In the spectrum, the chemical shifts of inimo and one amino protons are located in 10.5 to 12.0 ppm, showing that JG244 forms a stable G-quartet molecular structure. With the influence of G-quartet H-bond formation, the chemical shifts of all inimo protons should be located in 10 to 11.5 ppm, which are different with other DNA structures. Hydrogen bond formation of G-quartet bases is showed in left upper-panel.

Figure 23:
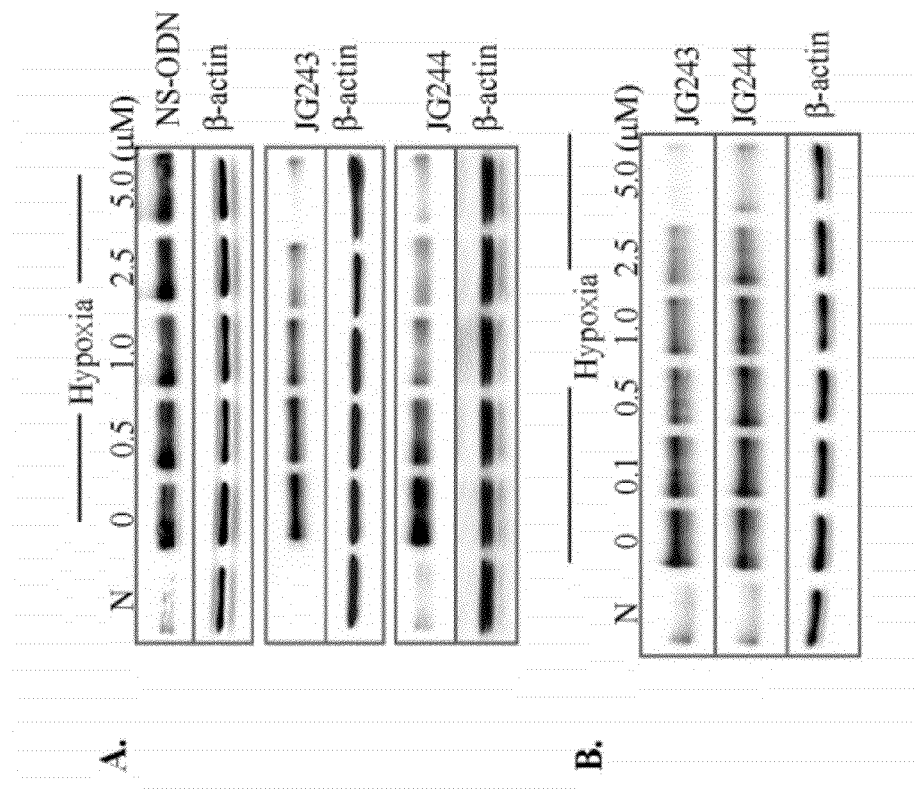
FIGS. 23A-23B show that JG243 and JG244 inhibit HIF-1α activation in (A) pancreatic and (B) prostate cancer cells.

JG243 and JG2444 Inhibit HIF-1α Activation in Pancreatic and Prostate Cancer Cells FIG. 23 shows that western blots demonstrated that in normoxic condition (Lane 1), HIF-1α was undetectable (HIF-1α has a short life-time of ~5 min, and is rapidly degraded by the ubiquitin-proteasome system). Under hypoxic condition, HIF-1α is not hydroxylated because the major substrate, dioxygen, is not available. The unmodified protein escapes the VHL-binding, ubiquitination, and degradation and dimerizes with HIF-1β and stimulates the transcription of its target genes. Comparing with the expression of HIF-1α without JG-ODNs (Lane 2), the $IC_{50}$s (50% inhibitory concentration) were determined by analysis of the intensities of HIF-1α peptide on the western blots. The $IC_{50}$s of JG243 and JG244 are ~1.5 to 2.0 µM in pancreatic cancer cells (A) and prostate cancer cells (B).

Figure 24:
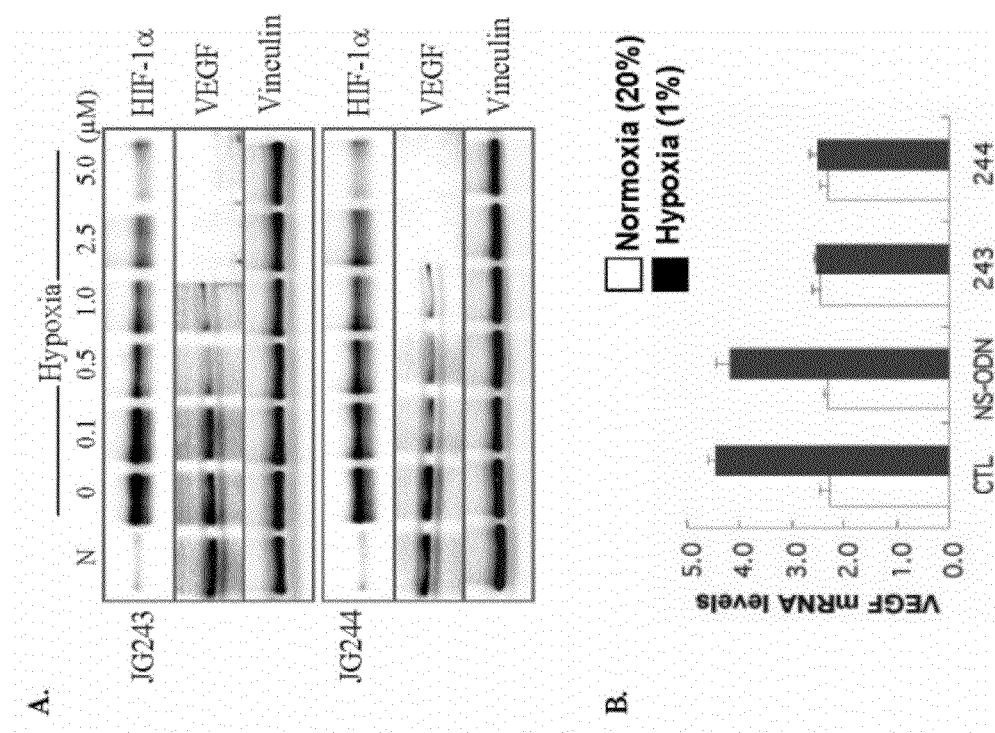
FIGS. 24A-24B show that JG-ODNs suppress the expression of (A) protein and (B) mRNA of VEGF, a HIF-1α downregulated protein.

JG-ODNs Suppress the Expression of Protein and mRNA of VEGF, and HIF-1α Down Regulated Protein To determine whether JG-ODNs can inhibit HIF-1α transcription under hypoxia, western blot and quantitative real time RT-PCR were performed to detect the mRNA and protein levels of a critical HIF-1α regulated genes, VEGF (FIG. 24). (A) The results show that JG-ODNs significantly suppressed the expression of VEGF under hypoxia when the activation of HIF-1α was inhibited by JG-ODNs. (B) The quantitative PCR data showed that (i) mRNA levels of VEGF in hypoxia is twice as high as in nomorxia; and (ii) JG243 and JG244 suppressed the expressions of mRNA of VEGF in hypoxia but not in normoxia. These observations show that JG-ODNs target HIF-1α and block its transcription in hypoxia, inhibiting VEGF activation. NS-ODN is a non-specific DNA as a control.

Figure 25:
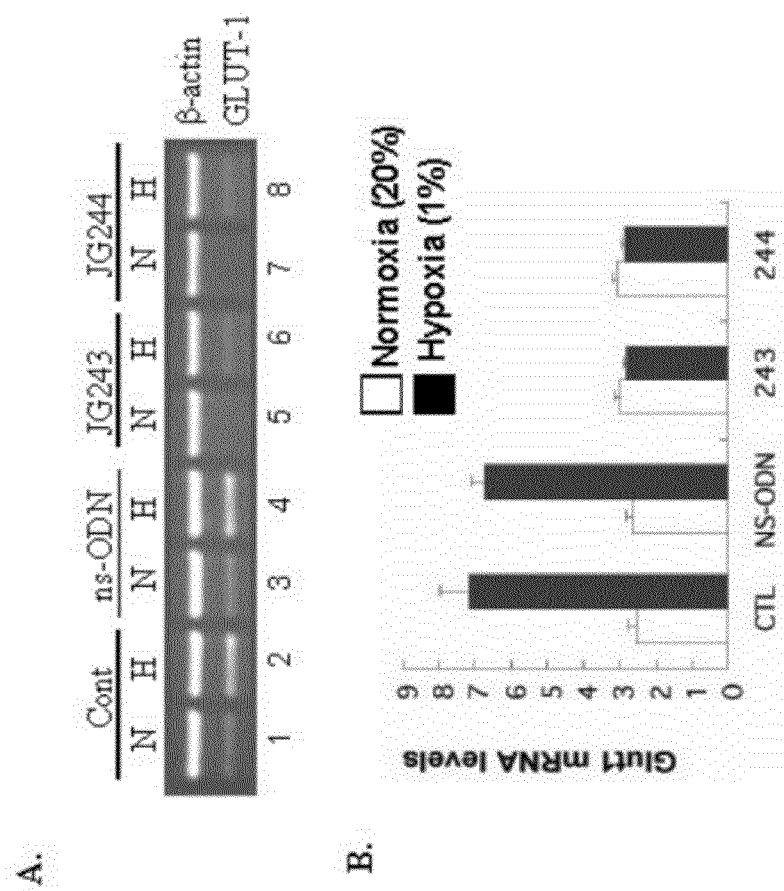
FIGS. 25A-25B show that JG-ODN suppress mRNA level of Glut 1 (glucose transporter 1), a HIF-1α regulated gene, in cancer cells.

JG-ODN Suppress mRNA Level of Glut1 (Glucose Transporter 1), a HIF-1α Regulated Gene, in Cancer Cells Quantitative real time RT-PCR was used to detect the mRNA levels of HIF-1α regulated genes, Glut-1 (FIG. 25). Three samples were used: ns-ODN/PEI (no-specific ODN as control); JG243/PEI; and JG244/PEI to test mRNA expression of GLUT1 in normoxia and hypoxia conditions. (A) The results of RT-PCR show that (i) GLUT-1 is more active in hypoxia than in normoxia (Lanes 1 & 2); (ii) compared to controls, ns-ODN has no suppressed mRNA of GlUT-1 (Lanes 3 & 4); and (iii) JG243 and JG244 strongly suppressed the expression of mRNA of GLUT-1. (B) The quantitative RT-PCR data showed that (i) mRNA levels of Glut-1 in hypoxia is twice as high as in nomorxia; (ii) JG243 and JG244 suppressed the expressions of mRNA of Glut1 in hypoxia but not in normoxia. The results are consistent and provide solid evidence that JG-ODNs specifically target HIF-1α and block its transcription in hypoxia.

JG243 and JG244 Block the Expressions of HIF-1α and HIF-2α, Bcl-2 and Bcl-$x_L$ But Did Not Disrupt the Activation of p53 in Cancer Cells.

Figure 26:
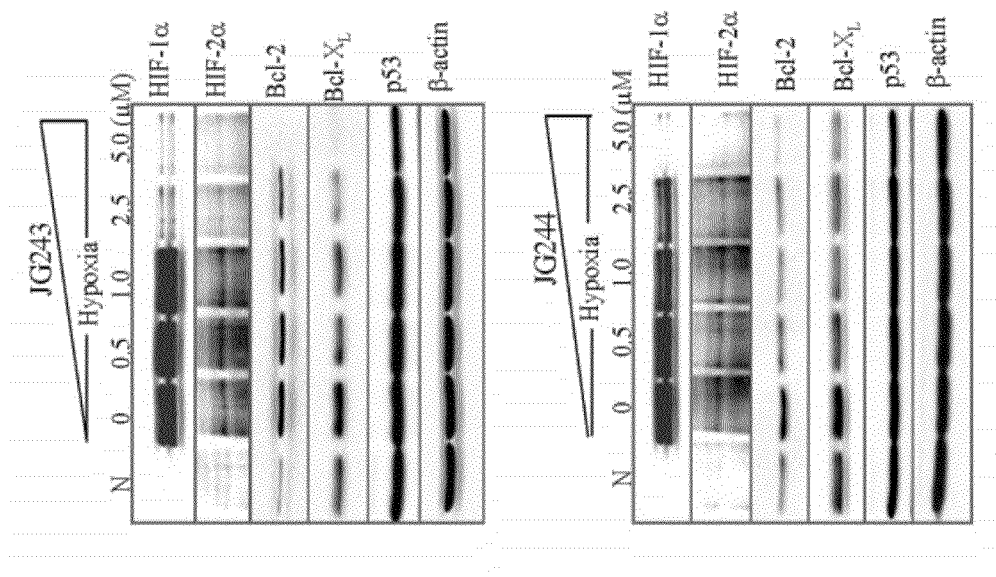
FIG. 26 shows JG243 and JG244 block the expression of HIF-1α and HIF-2α, Bcl-2 and Bcl-x$_L$ but did not disrupt the activation of p53 in cancer cells.

As shown in FIG. 26, western blots were performed to determine whether JG-ODNs inhibits the activations of HIF-2Oα, p53 and HIF-1α regulated proteins in pancreatic cancer cells. The results show that (i) under hypoxia both HIF-1α and HIF-2Oα are activated in cancer cells and the activations were significantly inhibited by JG243 and JG244. (ii) The expressions of the anti-apoptosis proteins, Bcl-2 and BCl-$X_L$, in hypoxia were 2 folds higher than that in normoxia, demonstrating hypoxic activation of anti-apoptosis. Their activations in hypoxia were strongly inhibited by JG243 and JG244. However, the activation of p53 (a tumor suppressor) was not disrupted by JG-ONDs. Together, JG-ODNs targeted HIF-1 and blocked their transcriptions, inducing increases of apoptosis and decreases of angiogenesis in cancer cells.

Drug Efficacy In Vivo

In vivo drug efficacy. In FIG. 27A, plots of tumor volumes versus days of drug treatment show that the growths of prostate, pancreatic and breast tumors were significantly suppressed by JG243 and JG244, respectively. The details of in vivo tests for JG-243 and JG 244 are summarized in Table 5.

TABLE 5

Summary of in vivo drug tests

| Cancer | Group | Drug dose | # of mice | | Weight of mice (g) | | Tumor (mm3) | | Weight of tumors (g) | p value |
| --- | --- | --- | --- | --- | --- | --- | --- | --- | --- | --- |
| | | | Start | End | Start | End | Start | End | | |
| PC-3 | Placebo (PEI) | 2.5 mg/kg | 4 | 4 | 18.8 ± 0.3 | 19.5 ± 0.8 | 10.1 ± 0.5 | 796 ± 86 | 0.58 ± 0.16 | |
| | JG243/PEI | 10 mg/kg + 2.5 mg/kg | 5 | 5 | 19.7 ± 0.3 | 20.8 ± 0.6 | 11.3 ± 2.8 | 103 ± 15 | 0.15 ± 0.07 | <0.02 |
| | JG244/PEI | 10 mg/kg + 2.5 mg/kg | 5 | 5 | 18.5 ± 0.4 | 19.4 ± 0.7 | 12.4 ± 1.6 | 98 ± 8.9 | 0.12 ± 0.03 | <0.02 |
| PANC-1 | Placebo (PEI) | 2.5 mg/kg | 4 | 4 | 20.5 ± 0.4 | 20.5 ± 0.5 | 34.8 ± 6.5 | 532 ± 110 | 0.36 ± 0.10 | |
| | JG243/PEI | 10 mg/kg + 2.5 mg/kg | 4 | 4 | 20.2 ± 0.5 | 20.9 ± 0.4 | 37.7 ± 5.4 | undetected | 0.02 ± 0.007 | <0.005 |
| | JG244/PEI | 10 mg/kg + 2.5 mg/kg | 4 | 4 | 21.3 ± 03 | 22.1 ± 0.2 | 25.6 ± 3.5 | 21 ± 7.0 | 0.07 ± 0.03 | <0.005 |
| MDA-468 | Placebo (PEI) | 2.5 mg/kg | 4 | 4 | 22.7 ± 0.3 | 24.5 ± 0.3 | 132 ± 27 | 510 ± 123 | 0.45 ± 0.05 | |
| | JG243/PEI | 10 mg/kg + 2.5 mg/kg | 5 | 5 | 24.2 ± 0.5 | 25.3 ± 0.2 | 127 ± 20 | 30.4 ± 12 | 0.04 ± 0.01 | <0.001 |
| | JG244/PEI | 10 mg/kg + 2.5 mg/kg | 5 | 5 | 22.9 ± 0.2 | 26.2 ± 0.4 | 91 ± 7.3 | 35.2 ± 17 | 0.03 ± 0.03 | <0.001 |

Drug efficacy for breast cancer (MDA-MB-468). To determine the drug efficacy for breast cancer, JG243 and JG244 was injected every three days over a 31 day period (FIG. 27B). Over the 31-days of drug treatment, the mean size of breast tumors (MDA-MB-468) in PEI-treated mice increased from 132.1 to 510.4 ($mm^3$). The mean sizes of breast tumors in the mice treated with JG243 and JG244 decreased from 126.9 to 30.4 ($mm^3$) and from 90.6 to 35.2 ($mm^3$), respectively. In addition, the mean tumor weight of PEI-treated mice was 0.45±0.10 g. The mean tumor weights of JG243- and JG244-treated mice were only 0.04±0.01 g and 0.03±0.05 g, respectively.

Figure 2:
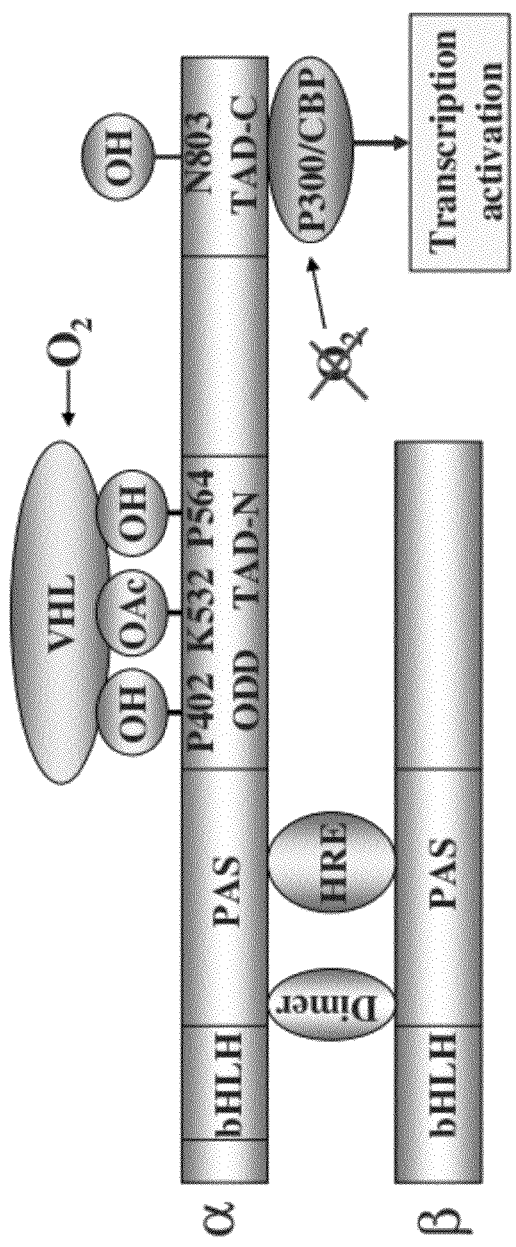
FIG. 2 illustrates molecular structures of HIF-1α and HIF-1β.
Figure 27:
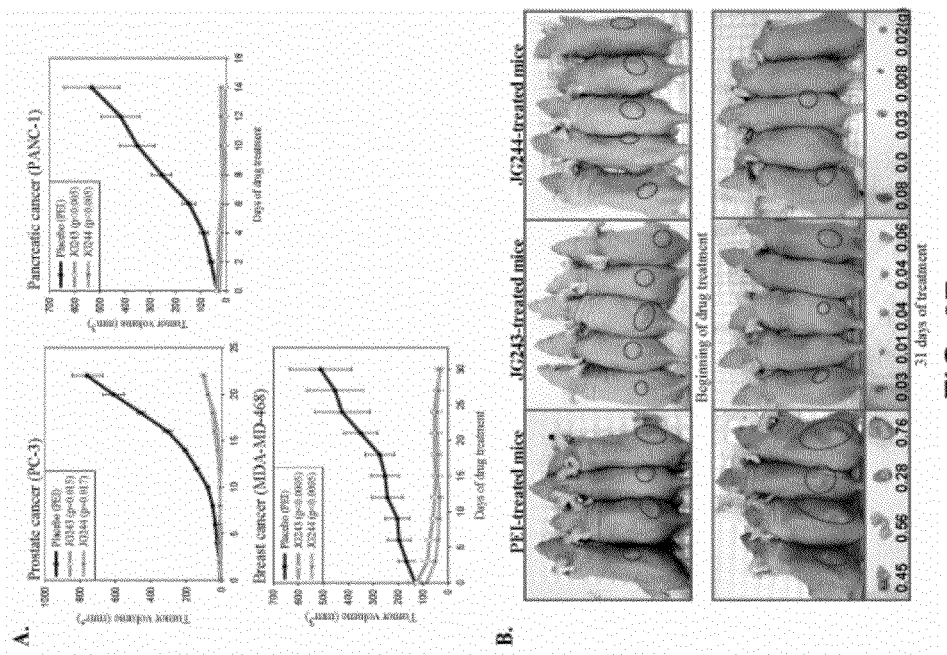
FIGS. 27A-27C show drug efficacy in vivo.
Figure 27:
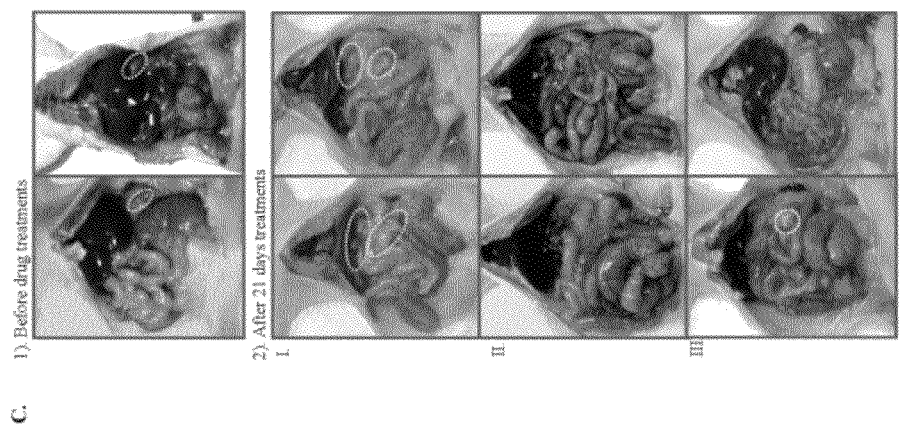

The treatment of the pancreatic tumors grown inside the bodies of nude mice (FIG. 27C). To determine whether JG243 and JG244 can significantly suppress the pancreatic tumor growth in the similar microenvironments of the patients with pancreatic cancers, pancreatic cancer cells (PANC-1) were injected inside bodies of nude mice through IP (intraperitoneal) injection. Each mouse was injected with $5 \times 10^6$ cells. After 8 days, two mice were randomly sacrificed and each mouse had grown small pancreatic tumor in pancreatic tissue (FIG. 27C1). Then, drug treatments began in three small groups: (i) PEI-treated only; (ii) JG243/PEI-treated; and (iii) JG244-treated mice. PEI alone (2.5 g/kg) and JG-ODN/PEI (10 mg/kg+2.5 mg/kg) was injected every two days for 21 days treatments. After the treatments, pancreatic tumors were found to be largely grown in bodies of PEI-treated mice (FIG. 27C2-I), however, pancreatic tumors were disappeared in the bodies of JG243-treated mice (FIG. 27C2-II) and one small pancreatic tumor was found in one body of JG244-treated mice (FIG. 27 C2-III). The results are consistent with data shown previously and provide solid evidence that JG-ODNs significantly suppress pancreatic tumor growth.

Example 5

Significance of the Present Invention

There is significance for developing a novel HIF-1 inhibitor for cancer therapy. (i)

In the year 2005, carcinoma of the prostate (for example) accounted for an estimated ~190,000 new cancer cases and more than 30,000 deaths in the United States. Prostate cancer is one of the most frequently diagnosed cancers and the second leading cause of cancer death in American men. Current treatments for androgen-independent prostate cancer have not shown a definitive increase in survival. The treatment options employed for patients with advanced and metastatic prostate cancer are limited. (ii) Pancreatic cancer is the fourth leading cause of cancer mortality in both men and women and remains a most formidable malignancy. Approximately 32,000 new cases of pancreatic cancer will be diagnosed in the United States each year, and the annual mortality rate closely approaches that of the number of new cases. Usually undiagnosed until reaching advanced stage, pancreatic cancer is characterized by its predisposition to aggressively invade surrounding tissues, to metastasize early and extensively, and to resist conventional chemoradiation treatment strategies.

Innovative treatment approaches employing new agents, with different mechanisms of action and novel molecular target, are urgently needed for human cancer therapy. Mounting evidence showed that a growing mass of tumor cells must recruit its own blood supply for maintenance of oxygen and nutrients, termed tumor angiogenesis. Within tumors, hypoxia serves as a critical factor for both physiological and pathological angiogenesis. In response to intratumoral hypoxia, angiogenesis-stimulating factors produced in tumor cells are critical for tumor cells to survive and proliferate in a hostile microenvironment. Thus, hypoxia-inducible factor-1 (HIF-1) is an important process in the progression and treatment resistance of many human cancers.

Figure 16:
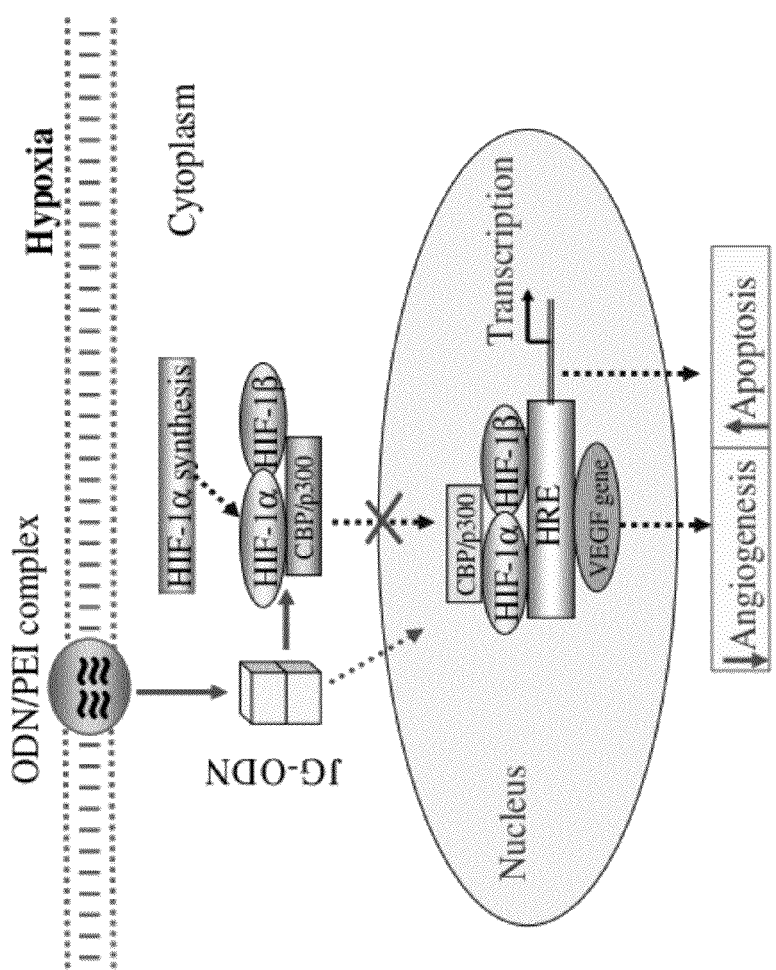
FIG. 16 shows an exemplary mechanism of inhibition of HIF-1α activation and transcription by JG-ODNs. HRE is Hypoxia-respond element.

A mechanism of JG-ODNs inhibiting HIF-1α activation is provided. HIF-1α has been identified as an important molecular target for cancer therapy since HIF-1α activates the transcription of genes that are involved in crucial aspects of cancer biology, including angiogenesis, cell survival, glucose metabolism and invasion. Therefore, targeting HIF-1α will constitute a novel and potent therapeutic treatment for human cancers. Under hypoxia conditions, synthesized HIF-1α is not hydroxylated because the major substrate, dioxygen, is not available. The unmodified protein escapes the VHL-binding, ubiquitination, and degradation, and then dimerizs HIF-1α and stimulates the transcription of its target genes. When $N_8O_3$ is not asparaginyl-hydroxylated, p300 and CBP can bind to HIF-1α, allowing transcriptional activation of HIF-1 target genes, which are involved in many cell processes: angiogenesis, anti-apoptosis, metabolism, metastasis, and others. The G-quartet ODNs, which were delivered by PEI, bound into the region of residue 796 to 806 of HIF-1α to inhibit the interaction between p300/CBP and $N_8O_3$ of HIF-1α and block its transcriptional activation under hypoxia (FIG. 16). Drug efficacies of JG243 and JG244 have been examined in vivo using nude mice xenografts. The results showed that both JG243 and JG244 significantly suppress the tumor masses and greatly reduce the rates of pancreatic and prostate tumor growths due to decreasing angiogenesis and increasing apoptosis. It is also noted that JG243 induced a negative rate for pancreatic tumor growth and totally killed the pancreatic tumors in all treated mice during a two-week period, showing a very powerful drug activity. Therefore, JG-ODNs have great capacity to be potent HIF-1α inhibitors and represent a novel and promising class of anti-cancer drugs in the treatment of pancreatic tumors.

In summary, the present invention provides the following embodiments for JG-ODNs, a novel and potent anti-cancer agent that targets HIF-1α for human cancer therapy:

(1) A rational model was constructed based on the NMR structure of the C-terminal of HIF-1α (Dames et al., 2002), and have established a structure-activity relationship (SAR) between JG-ODNs and HIF-1α for rational drug design. A drug optimization procedure was also established in order to increase the success rate of JG-ODN in future clinical trials.

(2) As lead compounds, JQ243 and JG244, which form an intramolecular G-quartet structure, are potent inhibitors of HIF-1α activation in human cancer cells, including pancreatic and prostate cancers. JG-ODNs also block the expression of HIF-1α down stream protein VEGF and significantly reduce angiogenesis and increase apoptosis in human cancers. The in vivo drug tests demonstrated that JG243 and JG244 significantly suppress the tumor masses and greatly reduce the rate of tumor growths, including breast, pancreatic and prostate cancers. Specially, JG243 induced a negative rate for pancreatic tumor growth and totally killed the pancreatic tumors in all treated mice during a two-week period, showing a very powerful drug activity.

(3) The stable G-quartet motifs are the primary determinants of the remarkable nuclease resistance and long-term biological efficacy of these oligonucleotides. The intramolecular G-quartet structure prevents single-strand endonucleases from accessing their cleavage sites, leading to a long oligonucleotide half-life in serum and inside cells (Bishop et al., 1996).

(4) A novel and effective intracellular delivery system for G-quartet ODNs was developed (Jing et al., 2002). Effective delivery of the GQ-ODNs into cancer cells is a key issue for success in cancer therapies. This system greatly increases delivery efficiency and drug activity of JG-ODNs within cells. This system has also demonstrated the capacity for G-quartet ODN delivery into animal tissues (Jing et al., 2005), which indicates strong promise for the future use of these agents in the treatment of metastatic cancers.

(5) G-rich ODNs are agents with low toxicity. Toxicity studies have been published for G-rich ODN T30177 (or AR177), an analog of JG-ODNs (Wallace et al., 2000). G-rich ODNs did not exhibit genetic toxicity in three different mutagenic assays: Ames/Salmonella mutagenesis assay, CHO/HGPRT mammalian cell mutagenesis assay, and mouse micronucleus assay. Acute toxicity studies in mice have shown that the G-rich ODN has an LD50 (lethal dose of 50%) at >1.5 g/kg body weight, which is higher than 150-fold of in vivo therapeutic levels. Multiple-dose toxicity studies in mice have reported that G-rich ODN does not cause male-specific mortality or changes in serum chemistry, hematology, and histology until doses reach 600 mg/kg, which are >60-fold greater than the therapeutic levels. Clinical chemistry findings have included changes in liver function and decreased erythrocyte values at 600 mg/kg.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Patents and Patent Applications

U.S. Pat. No. 4,162,282
U.S. Pat. No. 4,310,505
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 5,401,511
U.S. Pat. No. 5,603,872
U.S. Pat. No. 5,879,703
International Application PCT/US85/01161
International Application PCT/US89/05040
U.K. Patent Application GB 2193095 A Publications Bicknell R, Harris A L. Novel angiogenic signaling pathway and vascular targets. Annu. Rev. Phamacol. Toxicol. 2004; 44:219-238.

Bishop J S, Guy-Caffey J K, Ojwang J O, Smith S R, Hogan M E, Cossum P A, Rando R F, Chaudhary N. G-quartet motifs confer nuclease resistance to a potent anti-HIV oligonucleotide. J. Biol. Chem. 1996; 271:5698-57036.

Duffy J P, Eibl G, Reber H A, Hines O J. Influence of hypoxia and neoangiogenesis on the growth of pancreatic cancer. Mol. Cancer 2003, 2:12-22.

Brahimi-Horn C, Berra E, Pouyssegur J. Hypoxia: the tumor's gateway to progression along the angiogenic pathway. Trends Cell Biol. 2001; 11:S32-S36. doi: 10.1016/S0962-8924(01)02126-2.

Dames S A, Martinez-Yamout M, De Guzman R N, Dyson H J, Wright P E. Structural basis for Hif-1alpha/CBP recognition in the cellular hypoxic response. Proc. Natl. Acad. Sci. USA 2002; 99:5271-5276.

Folkman J. Tumor angiogenesis: therapeutic implications. N. Engl. J. Med 1971, 285:1182-1186.

Gatenby R A, Kessler H B, Rosenblum J S, Coia L R, Moldofsky P J, Hartz W H, Broder G J. Oxygen distribution in squamous cell carcinoma metastases and its relationship in outcome of radiation therapy. Int J Radiat Oncol Biol Phys 1988; 48:831-838.

Harris A L. Hypoxia-a key regulatory factor in tumor growth. Nat Rew Cancer 2002; 2:38-47.

Hirota K, Semenza G L. Regulation of angiogenesisi by hypoxia-inducible-factor-1. Crit Rev Oncol Hematol. 2006; 59(1):15-26.

Huang L E, Gu J, Schau M, Bunn H F. Regulation of hypoxia-inducible factor 1α is mediated by an $O_2$-dependent degradation domain via the ubiquitin-proteasome pathway. Poc Natl Acad Sci USA. 1998; 95:7987-7992. doi: 10.1073/pnas.95.14.7987.

Ikeda N, Adachi M, Taki T, Huang C, Hashida H, Takabayashi A, Sho M, Nakajima Y, Kanehiro H, Hisanaga M, Nakano H, Miyake M. Prognostic significance of angiogenesis in human pancreatic cancer. Br J Cancer. 1999; 79:1553-1563. doi: 10.1038/sj.bjc.6690248.

Jing N, Li Y, Xu X, Li P, Feng L, Tweardy D. Inhibitor of Stat3 Activity by G-quartet oligodeoxynucleotides. DNA and Cell Biology 2003; 22:685-696.

Jing N, Li Y, Xiong, W, Sha W, Jing L. Tweardy D J. G-quartet oligonucleotides: a new class of Stat3 inhibitors that suppresses growth of prostate and breast tumors through induction of apoptosis. Cancer Research 2004; 64:6603-6609.

Jing N, Sha W, Li Y, Xiong W, Twaerdy D J. Rational drug design of G-quartet DNA as anti-cancer agents. Curr. Pharma. Design 2005; 11:2841-2854.

Jing N, Zhu Q, Yuan P, Li Y, Mao L, Tweardy D J. Targeting Stat3 with G-quartet oligonucleotides: a potential novel therapy for head and neck cancer. Mol. Cancer Therapeutics 2006; 5:279-286.

Jing N, Rando R F, Pommier Y, and Hogan M E. Ion Selective Folding of Loop Domains in a Potent Anti-HIV Oligonucleotide. Biochemistry 1997; 36: 12498-12505.

Jing N and Hogan M E. Structure-Activity of Tetrad-forming Oligonucleotide as a Potent Anti-HIV Therapeutic Drug. The Journal of Biological Chemistry 1998; 273:34992-34999.

Jing N, De Clercq E, Rando R F, Pallansch, L, Lackman-Smith C, Lee S, and Hogan M E. Stability-Activity Relationships of a Family of G-tetrad forming Oligonucleotides as Potent HIV Inhibitors: A Basis for Anti-HIV Drug Design. The Journal of Biological Chemistry 2000; 275: 3421-3430.

Jing N, Marchand C, Liu J, Mitra R, Hogan M E, Pommier Y. Mechanism of Inhibition of HIV-1 Integrase by G-tetrad Forming Oligonucleotides in vitro. Journal of Biological Chemistry 2000; 275:21460-21467.

Jing N, Xiong W, Guan Y, Pallasch L, Wang S. Potassium Dependent Folding: A Key to Intracellular Delivery of G-quartet Oligonucleotides as HIV Inhibitors. Biochemistry 2002; 41:5397-5403.

Katchalski-Katzir E, Shariv I., Eisenstein M, Friesem A A, Aflalo C, Vakser I A. Molecular surface recognition: determination of geometric fit between proteins and their ligands by correlation techniques. Proc Natli Acad Sci USA 1992; 89:2195-9.

Khan A W, Dhillon A P, Hutchins R, Abraham A, Shah S R, Snooks S, Davidson B R. Prognostic significance of intra-tumoural microvessel density (IMD) in resected pancreatic and ampullary cancers to standard histopathological variables and survival. Eur Surg J Oncol. 2002; 28:637-644. doi: 10.1053/ejso.2002.1307.

Niedergethmann M, hildenbrand R, Wolf G, Verbeke C S, Richter A, Post S. Angiogenesis and cathepsin expression are prognostic factors in pancreatic adenocarcinoma after curative resection. Int J Pancreatol. 2000; 28:31-39.

Powis G, Kirkpatrick L. Hypoxia inducible factor-1 as cancer drug target. Mol Cancer Therap 2004; 3:647-654.

Ritchie D W, Kemp G J. Protein docking using spherical polar Fourier correlations. Proteins 2000; 39:178-94.

Salceda S, Caro J. Hypoxia-inducible factor 1α (HIF-1α) protein is rapidly degraded by the ubiquitin-proteasome system under normoxic conditions: its stabilization by hypoxic depends upon redox-induced changes. J Biol Chem. 1997; 272:22642-22647.

Semenza G L. Targeting HIF-1 for cancer therapy. Nat Rew Cancer 2003; 3:721-732.

Semenza, G. L. and G. L. Wang, A nuclear factor induced by hypoxia via de novo protein synthesis binds to the human erythropoietin gene enhancer at a site required for transcriptional activation, Mol Cell Biol 12 (1992), pp. 5447-5454.

Shi Y H, Fang W G. Hypoxia-inducible factor-1 in tumor angiogenesis. World J Gastroenterol 2004; 10:1082-1087.

Wallace T L, Gamba-Vitalo C, Loveday K S, Cossum P A. Acute, multiple-dose, and genetic toxicology of AR177, an anti-HIV oligonucleotide. Toxicol. Sci. 2000, 53:63-70.

Wang, G. L. and G. L. Semenza, Purification and characterization of hypoxia-inducible factor 1, J Biol Chem 270 (1995), pp. 1230-1237.

Wang, G. L., B. H. Jiang, E. A. Rue and G. L. Semenza, Hypoxia-inducible factor 1 is a basic-helix-loop-helix-PAS heterodimer regulated by cellular $O_2$ tension, Proc Natl Acad Sci USA 92 (1995), pp. 5510-5514.

Zhong H, DeMarzo A M, Laughner E, Lim M, Hilton D A, Zagzag D, Buechler P, Isaacs W B, Semenza G L, Simons J W. Overexpression of Hpoxia-inducible Factor 1 in common human cancers and their metastases. Cancer Res. 1999; 59:5830-5835.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating hyperproliferative disease in an individual, comprising delivering to the individual a therapeutically effective amount of one or more oligonucleotides, wherein said oligonucleotides comprise a G quartet and inhibit HIF1α, wherein said oligonucleotides comprise SEQ ID NO:8.

2. A method of treating hyperproliferative disease in an individual, comprising delivering to the individual a therapeutically effective amount of one or more oligonucleotides, wherein said oligonucleotides comprise a G quartet and inhibit HIF1α, wherein said oligonucleotides comprise SEQ ID NO:9.

3. The method of claim 1, wherein the hyperproliferative disease is cancer and the individual is delivered an additional cancer therapy.

4. The method of claim 3, wherein the additional cancer therapy comprises chemotherapy, immunotherapy, radiation, surgery, or a combination thereof.

5. The method of claim 1, wherein the hyperproliferative disease is pancreatic cancer.

6. The method of claim 1, wherein the hyperproliferative disease is prostate cancer.

7. The method of claim 1, wherein the hyperproliferative disease is breast cancer.

8. A method of intracellular delivery of a G-rich oligonucleotide comprising the steps of:
   denaturing the oligonucleotide, wherein the oligonucleotide comprises a sequence selected from the group consisting of SEQ ID NO:8, and SEQ ID NO:9;
   mixing the oligonucleotide with a lipid to form an oligonucleotide-lipid complex; and
   incubating the oligonucleotide-lipid complex with a cell, wherein the oligonucleotide is internalized into the cell.

9. The method of claim 8, under conditions wherein the internalized oligonucleotide is induced to form a G-quartet structure.

10. The method of claim 9, wherein the G-quartet structure enters the nucleus.

11. The method of claim 9, wherein the G-quartet structure inhibits HIF1α expression and/or activity.

12. The method of claim 2, wherein the hyperproliferative disease is cancer and the individual is delivered an additional cancer therapy.

13. The method of claim 12, wherein the additional cancer therapy comprises chemotherapy, immunotherapy, radiation, surgery, or a combination thereof.

14. The method of claim 2, wherein the hyperproliferative disease is pancreatic cancer.

15. The method of claim 2, wherein the hyperproliferative disease is prostate cancer.

16. The method of claim 2, wherein the hyperproliferative disease is breast cancer.

* * * * *

SEQUENCE LISTING

```
<160> NUMBER OF SEQ ID NOS: 13

<210> SEQ ID NO 1
<211> LENGTH: 16
<212> TYPE: DNA
<213> ORGANISM: Artificial Sequence
<220> FEATURE:
<223> OTHER INFORMATION: Primer

<400> SEQUENCE: 1
gggcgggcgg gcgggc                                                       16
```

```
<210> SEQ ID NO 2
<211> LENGTH: 14
<212> TYPE: DNA
<213> ORGANISM: Artificial Sequence
<220> FEATURE:
<223> OTHER INFORMATION: Primer

<400> SEQUENCE: 2
ggtgggtggg tggg                                                        14

<210> SEQ ID NO 3
<211> LENGTH: 14
<212> TYPE: DNA
<213> ORGANISM: Artificial Sequence
<220> FEATURE:
<223> OTHER INFORMATION: Primer

<400> SEQUENCE: 3
ggcgggcggg cggg                                                        14

<210> SEQ ID NO 4
<211> LENGTH: 14
<212> TYPE: DNA
<213> ORGANISM: Artificial Sequence
<220> FEATURE:
<223> OTHER INFORMATION: Primer

<400> SEQUENCE: 4
ggcgggtggg cggg                                                        14

<210> SEQ ID NO 5
<211> LENGTH: 14
<212> TYPE: DNA
<213> ORGANISM: Artificial Sequence
<220> FEATURE:
<223> OTHER INFORMATION: Primer

<400> SEQUENCE: 5
ggtgggcggg tggg                                                        14

<210> SEQ ID NO 6
<211> LENGTH: 14
<212> TYPE: DNA
<213> ORGANISM: Artificial Sequence
<220> FEATURE:
<223> OTHER INFORMATION: Primer

<400> SEQUENCE: 6
ggtgggcagg tggg                                                        14

<210> SEQ ID NO 7
<211> LENGTH: 14
<212> TYPE: DNA
<213> ORGANISM: Artificial Sequence
<220> FEATURE:
<223> OTHER INFORMATION: Primer

<400> SEQUENCE: 7
ggtgggtagg tggg                                                        14

<210> SEQ ID NO 8
<211> LENGTH: 14
<212> TYPE: DNA
<213> ORGANISM: Artificial Sequence
<220> FEATURE:
<223> OTHER INFORMATION: Primer
```

```
<400> SEQUENCE: 8
ggcgggcagg cggg                                                    14

<210> SEQ ID NO 9
<211> LENGTH: 14
<212> TYPE: DNA
<213> ORGANISM: Artificial Sequence
<220> FEATURE:
<223> OTHER INFORMATION: Primer

<400> SEQUENCE: 9
ggcgggtagg cggg                                                    14

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10
ggtaggtggg tagg                                                    14

<210> SEQ ID NO 11
<211> LENGTH: 14
<212> TYPE: DNA
<213> ORGANISM: Artificial Sequence
<220> FEATURE:
<223> OTHER INFORMATION: Primer

<400> SEQUENCE: 11
ggtaggcggg tagg                                                    14

<210> SEQ ID NO 12
<211> LENGTH: 14
<212> TYPE: DNA
<213> ORGANISM: Artificial Sequence
<220> FEATURE:
<223> OTHER INFORMATION: Primer

<400> SEQUENCE: 12
ggtaggcagg tagg                                                    14

<210> SEQ ID NO 13
<211> LENGTH: 14
<212> TYPE: DNA
<213> ORGANISM: Artificial Sequence
<220> FEATURE:
<223> OTHER INFORMATION: Primer

<400> SEQUENCE: 13
ggtaggtagg tagg                                                    14
```